US010155782B2

(12) United States Patent
Wang et al.

(10) Patent No.: US 10,155,782 B2
(45) Date of Patent: Dec. 18, 2018

(54) METHOD FOR FUNCTIONALIZING TRANSITION METAL DICHALCOGENIDES

(71) Applicant: ARIZONA BOARD OF REGENTS ON BEHALF OF ARIZONA STATE UNIVERSITY, Scottsdale, AZ (US)

(72) Inventors: Qing Hua Wang, Scottsdale, AZ (US); Ximo Chu, Tempe, AZ (US); Alexander Green, Scottsdale, AZ (US); Ahmed Yousaf, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 29 days.

(21) Appl. No.: 15/288,952

(22) Filed: Oct. 7, 2016

(65) Prior Publication Data

US 2017/0101428 A1  Apr. 13, 2017

Related U.S. Application Data

(60) Provisional application No. 62/238,447, filed on Oct. 7, 2015.

(51) Int. Cl.
| | |
|---|---|
| *C07F 11/00* | (2006.01) |
| *C09K 11/06* | (2006.01) |
| *C09K 11/02* | (2006.01) |
| *C09K 11/68* | (2006.01) |

(52) U.S. Cl.
CPC ............ *C07F 11/005* (2013.01); *C09K 11/02* (2013.01); *C09K 11/06* (2013.01); *C09K 11/681* (2013.01); *C09K 2211/183* (2013.01)

(58) Field of Classification Search
USPC ............................................. 556/57, 61, 63
See application file for complete search history.

(56) References Cited

PUBLICATIONS

Knirsch (ACS Nano; 9(6), 6018-6030; published on May 13, 2015).*
Smith (Advanced Materials; 2011, 23, 3944-3948) with supporting information.*
Hossain (Journal of the American Chemical Society, 2010, 132, 15399-15403).*
Wang, Q. H., Kalantar-Zadeh, K., Kis, A., Coleman, J. N. & Strano, M. S. Electronics and optoelectronics of two-dimensional transition metal dichalcogenides. Nat. Nanotechnol. 7, 699-712 (2012).
Radisavljevic, B., Radenovic, A., Brivio, J., Giacometti, V. & Kis, A. Single-layer MoS2 transistors. Nat. Nanotechnol. 6, 147-150 (2011).
Mak, K. F., McGill, K. L., Park, J. & McEuen, P. L. The valley Hall effect in MoS2 transistors. Science 344, 1489-1492 (2014).
Sundaram, R. S. et al. Electroluminescence in Single Layer MoS2. Nano Lett. 13, 1416-1421 (2013).
Mak, K. F., Lee, C., Hone, J., Shan, J. & Heinz, T. F. Atomically Thin MoS2: A New Direct-Gap Semiconductor. Phys. Rev. Lett. 105, (2010).
Splendiani, A. et al. Emerging Photoluminescence in Monolayer MoS2. Nano Lett. 10, 1271-1275 (2010).
Radisavljevic, B., Whitwick, M. B. & Kis, A. Integrated Circuits and Logic Operations Based on Single-Layer MoS2. ACS Nano 5, 9934-9938 (2011).
Shih, C.-J. et al. Tuning On-Off Current Ratio and Field-Effect Mobility in a MoS2—Graphene Heterostructure via Schottky Barrier Modulation. ACS Nano 8, 5790-5798 (2014).
Son, Y. et al. Layer Number Dependence of MoS2 Photoconductivity Using Photocurrent Spectral Atomic Force Microscopic Imaging. ACS Nano 9, 2843-2855 (2015).
Kibsgaard, J., Chen, Z., Reinecke, B. N. & Jaramillo, T. F. Engineering the surface structure of MoS2 to preferentially expose active edge sites for electrocatalysis. Nature Mater. 11, 963-969 (2012).
Kim, S. et al. High-mobility and low-power thin-film transistors based on multilayer MoS2 crystals. Nature Commun. 3, 1011 (2012).
Yin, Z. et al. Single-Layer MoS2 Phototransistors. ACS Nano 6, 74-80 (2011).
Yuchen, D., Han, L., Neal, A. T., Mengwei, S. & Ye, P. D. Molecular Doping of Multilayer MoS2 Field-Effect Transistors: Reduction in Sheet and Contact Resistances. IEEE Electron Device Lett. 34, 1328-1330 (2013).
Kuila, T. et al. Chemical functionalization of graphene and its applications. Prog. Mater. Sci. 57, 1061-1105 (2012).
Georgakilas, V. et al. Functionalization of Graphene: Covalent and Non-Covalent Approaches, Derivatives and Applications. Chemical Reviews 112, 6156-6214 (2012). .
Paulus, G. L. C., Wang, Q. H. & Strano, M. S. Covalent Electron Transfer Chemistry of Graphene with Diazonium Salts. Acc. Chem. Res. 46, 160-170 (2012).
Bahr, J. L. & Tour, J. M. Covalent chemistry of single-wall carbon nanotubes. J. Mater. Chem. 12, 1952-1958 (2002).
Strano, M. S. et al. Electronic structure control of single-walled carbon nanotube functionalization. Science 301, 1519-1522 (2003).
Jin, Z. et al. Click Chemistry on Solution-Dispersed Graphene and Monolayer CVD Graphene. Chem. Mater. 23, 3362-3370 (2011).
Englert, J. M. et al. Covalent bulk functionalization of graphene. Nature Chem. 3, 279-286 (2011).

(Continued)

*Primary Examiner* — Pancham Bakshi
(74) *Attorney, Agent, or Firm* — Greenberg Traurig, LLP

(57) ABSTRACT

Embodiments of the invention provide a lithium-free metal dichalcogenides functionalization method where a metal dichalcogenide including a surface of predominantly semiconducting 2H phase is reacted with an aryl diazonium salt by exposing at least a portion of transition metal dichalcogenide to the aryl diazonium salt in the absence of alkyl lithium or alkyl lithium. A substantial portion of the reaction of the at least one aryl diazonium salt with the at least one transition metal dichalcogenide occurs with the semiconducting 2H phase. The aryl diazonium salt can be 4-nitrobenzenediazonium tetrafluoroborate or 4-carboxybenzene diazonium tetrafluoroborate, and the metal dichalcogenide can be $MoS_2$. The semiconducting 2H phase of the transition metal dichalcogenide is derived directly from mechanical exfoliation such as mechanical cleaving and/or sonication.

10 Claims, 16 Drawing Sheets

(56) References Cited

PUBLICATIONS

Shih, C.-J. et al. Disorder Imposed Limits of Mono- and Bilayer Graphene Electronic Modification Using Covalent Chemistry Nano Lett. 13, 809-817 (2013).
Wang, Q. H., Shih, C.-J., Paulus, G. L. C. & Strano, M. S. Evolution of Physical and Electronic Structures of Bilayer Graphene upon Chemical Functionalization. J. Amer. Chem. Soc. 135, 18866-18875 (2013).
Yang, L. et al. Chloride Molecular Doping Technique on 2D Materials: WS2 and MoS2. Nano Lett. 14, 6275-6280 (2014).
Sarkar, D. et al. Functionalization of transition metal dichalcogenides with metallic nanoparticles: implications for doping and gas-sensing. Nano Lett. 15, 2852-2862 (2015).
Chou, S. S. et al. Ligand Conjugation of Chemically Exfoliated MoS2. J. Amer. Chem. Soc. 135, 4584-4587 (2013).
Kang, P., Wang, M. C. & Nam, S. Bioelectronics with two-dimensional materials. Microelectronic Engineering 161, 18-35 (2016).
Kalantar-zadeh, K. & Ou, J. Z. Biosensors Based on Two-Dimensional MoS2. ACS Sensors 1, 5-16 (2016).
Kalantar-zadeh, K. et al. Two-Dimensional Transition Metal Dichalcogenides in Biosystems. Adv. Funct. Mater. 25, 5086-5099 (2015).
Schmidt, H., Giustiniano, F. & Eda, G. Electronic transport properties of transition metal dichalcogenide field-effect devices: surface and interface effects. Chem. Soc. Rev. (2015).
Dhakal, K. P. et al. Confocal absorption spectral imaging of MoS2: optical transitions depending on the atomic thickness of intrinsic and chemically doped MoS2. Nanoscale 6, 13028-13035 (2014).
Mouri, S., Miyauchi, Y. & Matsuda, K. Tunable Photoluminescence of Monolayer MoS2 via Chemical Doping. Nano Lett. 13, 5944-5948 (2013).
Fang, H. et al. Degenerate n-Doping of Few-Layer Transition Metal Dichalcogenides by Potassium. Nano Lett. 13, 1991-1995 (2013).
Voiry, D. et al. Covalent functionalization of monolayered transition metal dichalcogenides by phase engineering. Nature Chem. 7, 45-49 (2015).
Knirsch, K. C. et al. Basal-Plane Functionalization of Chemically Exfoliated Molybdenum Disulfide by Diazonium Salts. ACS Nano 9, 6018-6030 (2015).
Liu, T. et al. Drug Delivery with PEGylated MoS2 Nano-sheets for Combined Photothermal and Chemotherapy of Cancer. Adv. Mater. 26, 3433-3440 (2014).
Yin, W. et al. High-Throughput Synthesis of Single-Layer MoS2 Nanosheets as a Near-Infrared Photothermal-Triggered Drug Delivery for Effective Cancer Therapy. ACS Nano 8, 6922-6933 (2014).
Sharma, R., Baik, J. H., Perera, C. J. & Strano, M. S. Anomalously Large Reactivity of Single Graphene Layers and Edges toward Electron Transfer Chemistries. Nano Lett. 10, 398-405 (2010).
Sharma, R., Nair, N. & Strano, M. S. Structure-Reactivity Relationships for Graphene Nanoribbons. J. Phys. Chem. C 113, 14771-14777 (2009).
Wang, Q. H. et al. Understanding and controlling the substrate effect on graphene electron-transfer chemistry via reactivity imprint lithography. Nature Chem. 4, 724-732 (2012).
Bahr, J. L. et al. Functionalization of Carbon Nanotubes by Electrochemical Reduction of Aryl Diazonium Salts: A Bucky Paper Electrode. J. Amer. Chem. Soc. 123, 6536-6542 (2001).
Hossain, M. Z., Walsh, M. A. & Hersam, M. C. Scanning Tunneling Microscopy, Spectroscopy, and Nanolithography of Epitaxial Graphene Chemically Modified with Aryl Moieties. J. Amer. Chem. Soc. 132, 15399-15403 (2010).
Wang, Q. H. & Hersam, M. C. Characterization and nanopatterning of organically functionalized graphene with ultrahigh vacuum scanning tunneling microscopy. MRS Bull. 36, 532-542 (2011).
Bekyarova, E. et al. Chemical Modification of Epitaxial Graphene: Spontaneous Grafting of Aryl Groups. J. Amer. Chem. Soc. 131, 1336-1337 (2009).
Niyogi, S. et al. Spectroscopy of Covalently Functionalized Graphene. Nano Lett. 10, 4061-4066 (2010).
Ryder, C. R. et al. Covalent functionalization and passivation of exfoliated black phosphorus via aryl diazonium chemistry. Nature Chem. 8, 597-602 (2016).
Lee, C. et al. Anomalous Lattice Vibrations of Single- and Few-Layer MoS2. ACS Nano 4, 2695-2700 (2010).
Mak, K. F. et al. Tightly bound trions in monolayer MoS2. Nature Mater. 12, 207-211 (2013).
Lin, Y. et al. Dielectric screening of excitons and trions in single-layer MoS2. Nano Lett. 14, 5569-5576 (2014).
Fan, X.-Y., Nouchi, R., Yin, L-C. & Tanigaki, K. Effects of electron-transfer chemical modification on the electrical characteristics of graphene. Nanotechnology 21, (2010).
Girard, H. A. et al. Surface properties of hydrogenated nanodiamonds: a chemical investigation. Phys. Chem. Chem. Phys. 13, 11517-11523 (2011).
Lin, Y.-C. et al. Wafer-scale MoS2 thin layers prepared by MoO3 sulfurization. Nanoscale 4, 6637-6641 (2012).
Kim, I. S. et al. Influence of Stoichiometry on the Optical and Electrical Properties of Chemical Vapor Deposition Derived MoS2. ACS Nano 8, 10551-10558 (2014).
Zhang, L. et al. Electronic structure and chemical bonding of a graphene oxide-sulfur nanocomposite for use in superior performance lithium-sulfur cells. Phys. Chem. Chem. Phys. 14, 13670-13675 (2012).
Huang, Y. et al. Sulfurized activated carbon for high energy density supercapacitors. J. Power Sources 252, 90-97 (2014).
Cunningham, G. et al. Solvent Exfoliation of Transition Metal Dichalcogenides: Dispersibility of Exfoliated Nanosheets Varies Only Weakly between Compounds. ACS Nano 6, 3468-3480 (2012).
Backes, C. et al. Functionalization of Liquid-Exfoliated Two-Dimensional 2H-MoS2. Angew. Chemie Int. Ed. 54, 2638-2642 (2015).
Eda, G. et al. Photoluminescence from Chemically Exfoliated MoS2. Nano Lett. 11, 5111-5116 (2011).
Liang, Y., Thorne, J. E. & Parkinson, B. A. Controlling the Electronic Coupling between CdSe Quantum Dots and Thiol Capping Ligands via pH and Ligand Selection. Langmuir 28, 11072-11077 (2012).
Lu, Y. et al. Graphene-protein bioelectronic devices with wavelength-dependent photoresponse. Appl. Phys. Lett. 100, 033110 (2012).
Cheng, L. et al. PEGylated WS2 Nanosheets as a Multifunctional Theranostic Agent for in vivo Dual-Modal CT/Photoacoustic Imaging Guided Photothermal Therapy. Adv. Mater. 26, 1886-1893 (2014).
Ou, J. Z. et al. Ion-Driven Photoluminescence Modulation of Quasi-Two-Dimensional MoS2 Nanoflakes for Applications in Biological Systems. Nano Lett. 14, 857-863 (2014).
Nair, N., Kim, W.-J., Usrey, M. L. & Strano, M. S. A Structure-Reactivity Relationship for Single Walled Carbon Nanotubes Reacting with 4-Hydroxybenzene Diazonium Salt. J. Amer. Chem. Soc. 129, 3946-3954 (2007).
Koehler, F. M., Jacobsen, A., Ensslin, K., Stampfer, C. & Stark, W. J. Selective Chemical Modification of Graphene Surfaces: Distinction Between Single- and Bilayer Graphene. Small 6, 1125-1130 (2010).
Zhou, W. et al. Intrinsic Structural Defects in Monolayer Molybdenum Disulfide. Nano Lett. 13, 2615-2622 (2013).
Hong, J. et al. Exploring atomic defects in molybdenum disulphide monolayers. Nature Commun. 6, (2015).
Mignuzzi, S. et al. Effect of disorder on Raman scattering of single-layer MoS2. Phys. Rev. B 91, 195411 (2015).
Pollard, A. J. et al. Quantitative characterization of defect size in graphene using Raman spectroscopy. Appl. Phys. Lett. 105, 253107 (2014).
Lucchese, M. M. et al. Quantifying ion-induced defects and Raman relaxation length in graphene. Carbon 48, 1592-1597 (2010).
Jiang, D.-e., Sumpter, B. G. & Dai, S. How Do Aryl Groups Attach to a Graphene Sheet? J. Phys. Chem. B 110, 23628-23632 (2006).
Nečas, D. & Klapetek, P. Gwyddion: an open-source software for SPM data analysis. Cent. Eur. J. Phys. 10, 181-188 (2012).
Saby, C., Ortiz, B., Champagne, G. Y. & Bélanger, D. Electrochemical Modification of Glassy Carbon Electrode Using Aromatic Diazonium

(56) References Cited

PUBLICATIONS

Salts. 1. Blocking Effect of 4-Nitrophenyl and 4-Carboxyphenyl Groups. Langmuir 13, 6805-6813 (1997).

Green, Alexander A., Silver, Pamela A., Collins, James J. & Yin, P. Toehold Switches: De-Novo-Designed Regulators of Gene Expression. Cell 159, 925-939 (2014).

Ferrari, A. C. & Basko, D. M. Raman spectroscopy as a versatile tool for studying the properties of graphene. Nat. Nanotechnol. 8, 235-246 (2013).

Xue, J. M. X. J. M. et al. Scanning tunnelling microscopy and spectroscopy of ultra-flat graphene on hexagonal boron nitride. Nature Mater. 10, 282-285 (2011).

Chow, P. K. et al. Defect-Induced Photoluminescence in Monolayer Semiconducting Transition Metal Dichalcogenides. ACS Nano 9, 1520-1527 (2015).

Addou, R. et al. Impurities and Electronic Property Variations of Natural MoS2 Crystal Surfaces. ACS Nano 9, 9124-9133 (2015).

Wang, C. et al. Electronically Selective Chemical Functionalization of Carbon Nanotubes: Correlation between Raman Spectral and Electrical Responses. J. Amer. Chem. Soc. (2005).

Zhao, P. et al. Air Stable p-Doping of WSe2 by Covalent Functionalization. ACS Nano 10, 10808-10814 (2014).

Shaoo, J. K. Surface Functionalization of Metal Chalcogenides, 2011. Ph.D. dissertation, Johannes Gutenberg University in Mainz.

Chu, X. et al. Direct Covalent Chemical Functionalization of Pristine Molybdenum Disulfide Monolayers and Bilayers. (2015).

Chu, X. S. et al. Lithium-Free Direct Covalent Chemical Functionalization of Pristine Two-Dimensional Molybdenum Disulfide. (2016).

Guardia, L. et al. Production of aqueous dispersions of inorganic graphene analogues by exfoliation and sabilzation with non-ionic surfactants. RCS Advances 4, 14114-14127 (2014).

Castellanos-Gomez, A., van der Zant, H.S. J. & Steele, G. A. Folded MoS2; layers with reduced interlayer coupling. Nano Research 7, 572-578 (2015).

Liu, K. et al. Evolution of interlayer coupling in twisted molybdenum disulfide bilayers. Nature communications 5, 4966 (2014).

Crowne, F.J. et al. Blueshift of the A-exciton peak in folded monolayer 1H-MoS2. Physical Review B 88, (2013).

Li, H. et al. Optoelectronic crystal of artificial atoms in strain-textured molybdenum disulphide. Nature communications 6, (2015).

Radisavljevic, B., Radenovic, A., Brivio, J., Giacometti, V. & Kis, A. Single-layer MoS2 transistors. Nature Nanotechnology 6, 147-150 (2011).

Li, H. et al. Fabrication of Single- and Nultilayer MoS Film-Based Field-Effect Transistors for Sensing NO at Room Temperature. Small 8, 63-67 (2012).

Addou, R., Colombo, L. & Wallace, R. M. Surface Defects on Natural MoS. ACS Applied Materials & Interfaces 7, (2015). 11921-11929 (2015).

Santosh, K. C., Roberto, C. L., Rafik, A., Robert, M. W. & Kyeongjae, C. Impact of intrinsic atomic defects on the electronic structure of MoS monolayers. Nanotechnology 25, 375703 (2014).

Chakraborty, B. et al. Symmetry-dependent phonon renormalization in monolayer MoS2 transistor. Physical Review B 85, 161403 (2012).

Tongay, S. et al. Defects activated photoluminescence in two-dimensional semiconductors: interplay between bound, charged, and free excitons. Scientific reports 3, 2657 (2013).

\* cited by examiner 30 min

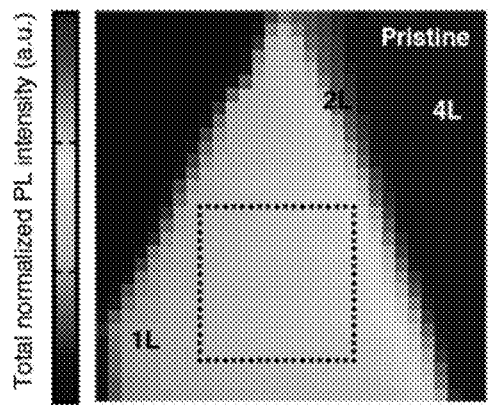 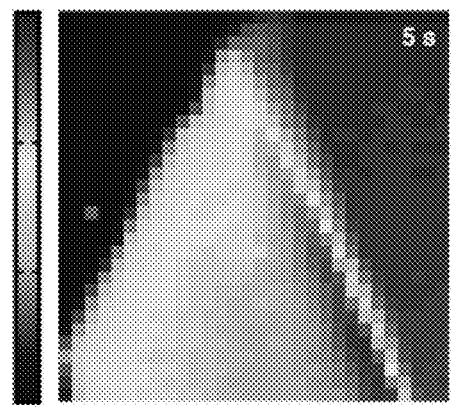
FIG. 3E          FIG. 3F
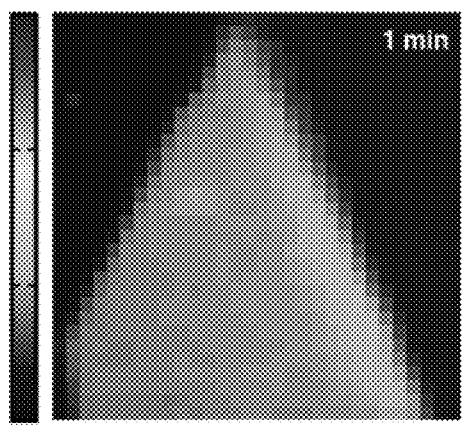 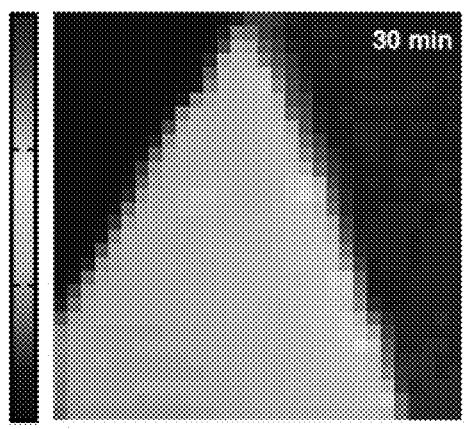
FIG. 3G          FIG. 3H

METHOD FOR FUNCTIONALIZING TRANSITION METAL DICHALCOGENIDES

RELATED APPLICATIONS

This application claims priority to U.S. provisional application Ser. No. 62/238,447, filed on Oct. 7, 2015, the entire contents of which are incorporated herein by reference.

BACKGROUND

Two-dimensional semiconducting transition metal dichalcogenides ("TMDCs") have generated significant research activity and excitement in the past few years due to their promising and intriguing properties, such as layer number dependent band gaps, photoluminescence, electroluminescence, valley polarization, and catalytic activity. For other low-dimensional materials such as carbon nanotubes and graphene, chemical functionalization has been crucial for modifying their physical, electronic, optical, and chemical properties. By using chemistry to tune these properties, it is possible to engineer how these materials behave, and how they interact with their external environment for a wide range of applications including transistors and gas sensors. The chemical functionalization of TMDCs is expected to be similarly important, yet methods for doing so are in their relative infancy. Noncovalent doping of TMDCs has been demonstrated using various chemical species such as potassium, polyethyleneimine (PEI), 1,2-dichloroethane, benzyl viologen (BV), and $F_4TCNQ$ and NADH; meanwhile, covalent functionalization of the basal plane has been demonstrated using organic halides and aryl diazonium salts, as well as thiolation of chalcogen vacancies.

Covalent functionalization is beneficial for many applications because the chemical changes are more robust and stable. Previous reports of covalent functionalization have relied on first converting the semiconducting 2H phase of $MoS_2$, $WS_2$, and $MoSe_2$ to the metallic 1T phase using n-butyllithium intercalation and exfoliation, (see for example the procedures described in Knirsch, K. C. et al. Basal-Plane Functionalization of Chemically Exfoliated Molybdenum Disulfide by Diazonium Salts. ACS Nano 9, 6018-6030 (2015), and in Voiry, D. et al. Covalent functionalization of monolayered transition metal dichalcogenides by phase engineering. Nature Chemistry 7, 45-49 (2015).) The lithiated forms of the TMDCs are more electron-rich, making them more amenable to some types of reactions, but they lose their semiconducting nature and photoluminescence (PL). The PL can be recovered after chemical functionalization, but at a different energy, suggesting the electronic structure is altered. Furthermore, processing using n-butyllithium is extremely hazardous because it is pyrophoric, corrosive, and flammable.

SUMMARY

Some embodiments include a lithium-free metal dichalcogenides functionalization method comprising providing at least one transition metal dichalcogenide comprising a surface of predominantly semiconducting 2H phase, and reacting at least a portion of the at least one transition metal dichalcogenide with the at least one aryl diazonium salt by exposing at least a portion of the at least one transition metal dichalcogenide to at least one aryl diazonium salt in the absence of alkyl lithium or alkyl lithium. A substantial portion of the reaction of the at least one aryl diazonium salt with the at least one transition metal dichalcogenide occurs with the semiconducting 2H phase.

In some embodiments of the invention, the at least one aryl diazonium salt comprises 4-nitrobenzenediazonium tetrafluoroborate. In other embodiments, the at least one aryl diazonium salt comprises 4-carboxybenzenediazonium tetrafluoroborate. In some embodiments, the semiconducting 2H phase of the at least one transition metal dichalcogenide is derived directly from mechanical exfoliation of the at least one transition metal dichalcogenide.

In some embodiments, the mechanical exfoliation is performed using sonication. In some embodiments, the at least one transition metal dichalcogenide is $MoS_2$. In some further embodiments, the $MoS_2$ reacts with the at least one aryl diazonium salt without prior conversion of the semiconducting 2H phase to metallic 1T phase.

In some embodiments, the at least one aryl diazonium salt comprises an aqueous solution of the aryl diazonium salt. In some further embodiments, the at least one transition metal dichalcogenide is dispersed in the aqueous solution. Some embodiments include the at least one transition metal dichalcogenide dispersed with at least one surfactant. In some embodiments, the at least one surfactant is sodium dodecyl sulfate.

Some embodiments of the invention include a $MoS_2$ modification method comprising forming basal plane $MoS_2$ surfaces by mechanically exfoliating bulk $MoS_2$ crystal, forming an aqueous solution of at least one aryl diazonium salt, and directly reacting the basal plane $MoS_2$ surfaces with the at least one aryl diazonium salt by exposure to the aqueous solution, wherein the reaction is a direct reaction of 2H phase $MoS_2$ to $MoS_2$ with covalently attached nitrophenyl groups.

In some embodiments, the direct reaction of the basal plane $MoS_2$ surfaces occurs in the absence of any lithium compound comprising lithium-carbon bonds. In some embodiments, the basal plane $MoS_2$ surfaces are dispersed in the aqueous solution. In some embodiments, the basal plane $MoS_2$ surfaces are produced by sonication of the aqueous solution. Some further embodiments include the aqueous solution with at least one surfactant. In some embodiments, the at least one surfactant comprises sodium dodecyl sulfate.

In some embodiments of the invention, the at least one aryl diazonium salt comprises 4-nitrobenzenediazonium tetrafluoroborate. In some embodiments, the at least one aryl diazonium salt comprises 4-carboxybenzenediazonium tetrafluoroborate. In some embodiments, the basal plane $MoS_2$ surfaces are sonicated during the exposure to the aqueous solution.

DESCRIPTION OF THE DRAWINGS

FIGS. 3E-3H shows raman peaks with spatial maps as a function of reaction time in accordance with some embodiments of the invention.

DETAILED DESCRIPTION

Figure 1A:
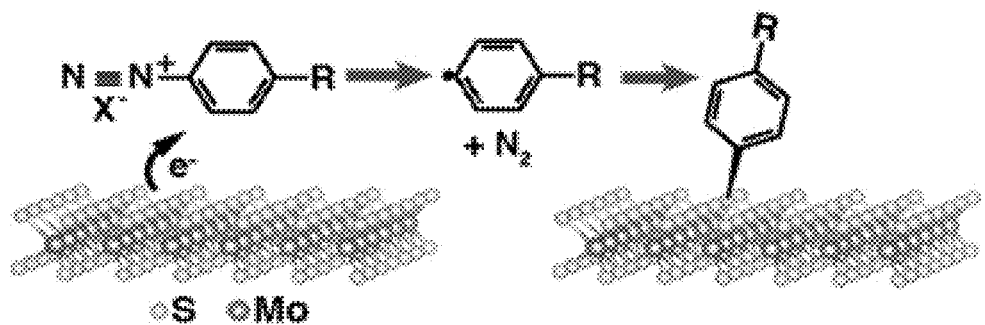
FIG. 1A illustrates covalent functionalization of $MoS_2$ by aryl diazonium salts in accordance with some embodiments of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The uses of "including," "comprising," or "having" and variations thereof herein are meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Some embodiments of the invention include direct covalent functionalization of pristine $MoS_2$ using aryl diazonium salts without the need for defect or phase engineering. For example, some embodiments of the invention include direct covalent functionalization of pristine $MoS_2$ monolayers and bilayers using aryl diazonium salts. Some of the embodiments described herein include the use of pristine mechanically exfoliated $MoS_2$ sheets that retain their attractive physical and electronic structures. Various materials produced by the methods as described herein are characterized using various analysis tools including X-ray photoemission spectroscopy ("XPS"), confirming the formation of S—C bonds during the covalent diazonium reaction. Further, using a combination of atomic force microscopy ("AFM") and Raman/photoluminescence ("PL") mapping, the detail the progress of the functionalization (over reaction times from 2 seconds to 6 hours) can be illustrated. In some embodiments, the PL analysis shows that the materials produced by the methods described include 2H phase $MoS_2$ that increases by up to two-fold for short reaction times, indicating changes in charge carrier density. The PL intensity subsides over longer reaction times due to increasing lattice disorder and activation of non-radiative recombination pathways. AFM imaging of surface coverage at different reaction times suggests a surface-limited reaction mechanism, and differences in reactivity can be observed for different layer numbers and at the edges of the flakes.

In some further embodiments, active protein molecules can be covalently tethered to functionalized $MoS_2$ surfaces prepared by alternative embodiments of the invention. For example, in some further embodiments of the invention, $MoS_2$ surfaces can be functionalized with carboxylic acid groups. In some embodiments, proteins can be reactively coupled to the carboxylic acid group functionalized $MoS_2$ surfaces. The covalent functionalization of $MoS_2$ by aryl diazonium salts is schematically illustrated in FIG. 1A. In some embodiments, the reaction process can begin with electron transfer from the filled states of $MoS_2$ to the empty states of the diazonium molecule. This results in the formation of an aryl radical and loss of a nitrogen molecule. The radical is very reactive and will readily form a covalent bond with the surface. The initial electron transfer step relies on the overlap of filled states in the substrate with empty states in the molecule, and thus the electronic structure and doping level of the substrate determines the reactivity.

In some embodiments of the invention, 4-nitrobenzenediazonium (4-NBD) tetrafluoroborate salt in aqueous solution can be used to functionalize mechanically exfoliated sheets of atomically thin $MoS_2$. In some embodiments, $SiO_2$ (300 nm)/Si substrates (Wafernet, Inc.) were ultrasonically cleaned in sequential baths of acetone and isopropanol and then blown dry with ultrahigh purity nitrogen gas. $MoS_2$ flakes were prepared on the cleaned substrate by mechanical exfoliation from a bulk $MoS_2$ crystal (SPI Supplies) using adhesive tape. The samples were then annealed in vacuum at 300° C. to remove tape residue. Monolayer, bilayer, and few-layer flakes were identified by optical microscopy and Raman spectroscopy. Other embodiments can include sonication of $MoS_2$ bulk material to introduce plane cleavage to produce 2H phase exposure sites. Further, some embodiments include diazonium functionalization of $MoS_2$. $MoS_2$ samples supported on $SiO_2$/Si substrates were immersed in 10 mM aqueous solutions of 4-nitrobenzenediazonium tetrafluoroborate (Sigma Aldrich) with constant stirring for defined reaction times. After each reaction step, the sample was gently rinsed with ultrapure water and blown dry with ultrahigh purity nitrogen gas before characterization.

In some embodiments, samples were characterized using Atomic force microscopy imaging. For example, in some embodiments, AFM imaging was conducted using a Multimode V system (Bruker Corp.) with ScanAsyst-Air tips (Bruker) in ScanAsyst noncontact mode. Raman and photoluminescence spectroscopy and mapping was used to characterize some embodiments of the invention. For example, in some embodiments, Raman and photoluminescence (PL) spectroscopy were performed in air at room temperature on a WITec alpha300R confocal Raman microscope system using a 532 nm excitation laser, 100× objective lens with ~1 μm diameter spot size. The laser power was kept between 0.26 to 0.32 mW to avoid damaging the $MoS_2$. The integration times were 1 s. Spatial maps of Raman and PL spectra were acquired at 30 pixels×30 pixels, using the 300 grooves/mm grating for the PL spectra and the 1800 grooves/mm grating for the Raman spectra. The peak positions, total area intensities, and widths are obtained by Lorentzian fits of the spectra using Matlab. The error of the peak position from fitting is estimated to be ~0.5 $cm^{-1}$.

Samples of continuous $MoS_2$ for x-ray photoelectron spectroscopy were prepared on $SiO_2$/Si substrates using chemical vapor deposition, and were sonicated in sequential baths of acetone and isopropanol for 5 minute each, blown dry with ultrahigh purity nitrogen gas, and cleaned in oxygen plasma (Harrick Plasma) at high power for 10 minute. Solid powder precursors $MoO_3$ (15 mg, Sigma-Aldrich, 99%) and S (100 mg, Alfa Aesar, 99.5%) were loaded into separate quartz boats (MTI Corp.) and placed into a 1" diameter quartz tube in a hot-wall tube furnace (Lindberg). The $MoO_3$ boat was positioned in the center of the furnace with the target $SiO_2$/Si substrate placed face down across the upper edges of the boat. The S boat was positioned at the edge of the heating zone where the temperatures reaches about 170° C. during growth. The quartz tube was pumped down to ~6 mtorr vacuum before flowing 300 sccm of ultrahigh purity Ar gas, so that the chamber pressure was ~1.35 torr during growth. The furnace was heated from room temperature to 650° C. over 40 minutes, kept at 650° C. for 30 minutes, and then cooled rapidly by shutting off the furnace and then cooling with an external fan. This growth procedure results in relatively large area, continuous and uniform coverage of multilayer $MoS_2$. The samples are left on the $SiO_2$/Si substrates and directly used in the XPS measurements. The four diazonium-functionalized samples were reacted for different reaction times (10 seconds, 5 minutes, 10 min, and 6 hours) and rinsed with ultrapure water and blown dry with ultrapure nitrogen gas before XPS measurement; the nitrobenzene control samples were dipped into nitrobenzene for 4 h and rinsed with isopropanol and dried before XPS measurement.

In some embodiments, samples were characterized using X-ray photoelectron spectroscopy (XPS). XPS spectra were acquired using a Vacuum Generators 220i-XL system with monochromated Al Kα radiation (hv=1486.6 eV), linewidth 0.7 eV, spot size ~400 μm, and chamber pressure ~$10^{-9}$ torr or lower. Spectra were analyzed using the CasaXPS software package to subtract the Shirley backgrounds and fit the peaks to Gaussian/Lorentzian functions. Peak positions were shifted using the Si 2p peak from the substrate as a reference. Peaks were identified by comparison to known standards and the La Surface database from Centre national de la recherche scientifique (CNRS) at Orleans, France, and ThermoFisher Scientific (www.lasurface.com).

Some embodiments include preparation of $MoS_2$ dispersions and functionalization in solution. Some embodiments include preparation of aqueousbased $MoS_2$ dispersions and functionalization in aqueous solution. For example, in some embodiments, $MoS_2$ was dispersed in sodium dodecyl sulfate (SDS) solution by probe sonicating 8.25 g of $MoS_2$ in 110 mL of 1% SDS solution (w/v) for 2 hours in a 250 mL steel beaker at 50% amplitude (power output of 48-50 W) using a Branson Digital Sonifier 450D. Then 25 mL of this dispersion were transferred in 4 separate 50 mL plastic tubes and centrifuged at 4200 rpm for 3.5 hours to remove large, undispersed particles. The resulting $MoS_2$-SDS dispersion is a very dark greenish color. To carry out the functionalization, 100 mg of the diazonium salt was added to 20 mL of the $MoS_2$-SDS dispersion and sonicated for 2 hours at 20% amplitude in a 50 mL tube. The resulting functionalized dispersion was flocculated with ethanol and filtered over hydrophilic PTFE membrane (Omnipore, 100 nm pore size) and washed thoroughly with water and ethanol.

In some embodiments, samples were characterized using FTIR and UV-VIS characterization of bulk dispersions of $MoS_2$. In some embodiments, the dried films of functionalized $MoS_2$ on filter membrane were used to collect Fourier transform infrared (FTIR) spectra. FTIR spectra were collected on Nicolet 6700 equipped with a Smart Orbit accessary. Then to re-suspend the samples in solution, the filter membranes were placed in 50 mL tubes along with 15 mL of SDS solution and sonicated for 2 hours. After sonication, the dispersions were filtered using Millipore vacuum filtration system (20 µm pore size) and then their UV-Vis absorbance spectra were collected (Jasco V760 UV-Visible/NIR Spectrophotometer). A control sample was also prepared in parallel, and instead of the functionalization with diazonium salt, it was just sonicated under the same conditions as above.

Thermogravimetric analysis (TGA) was used to analyze $MoS_2$ dispersions. In some embodiments, to prepare samples for TGA, 10 mL of the $MoS_2$ dispersion after 4-NBD functionalization was mixed with acetone in a ratio of 1:5 to aggregate and remove the SDS surfactant. After aggregation, the resulting dispersion was centrifuged for 30 minutes at 5000 rpm. The supernatant was decanted and the mixture was washed with 40 mL of DI water. The washing step was repeated three times. After washing, the sample was freeze dried to obtain a solid green powder, which was then analyzed using TGA. A control sample of the SDS-dispersed $MoS_2$ (without diazonium functionalization) was similarly processed to obtain solid green powder for TGA analysis. In some embodiments, TGA characterization was performed using a Setaram TG92 system. Each sample was purged with ultrahigh purity He gas overnight before TGA measurement. The He gas flow rate during the purge and the measurement was 30 mL per minute. The heating ramp rate was 5° C. per minute up to 900° C. The first derivative curve (DTG) was calculated in Matlab by first smoothing the TG curve using a Savitzky-Golay filter and then taking the numerical derivative.

Some embodiments include 4-carboxybenzenediazonium tetrafluoroborate synthesis and characterization and reaction with $MoS_2$ surfaces. In some embodiments, 4-carboxybenzenediazonium tetrafluoroborate (4-CBD) was synthesized following a reported procedure described in Saby, C., Ortiz, B., Champagne, G. Y. & Belanger, D. Electrochemical Modification of Glassy Carbon Electrode Using Aromatic Diazonium Salts. 1. Blocking Effect of 4-Nitrophenyl and 4-Carboxyphenyl Groups. Langmuir 13, 6805-6813 (1997), the entire contents of which is incorporated by reference. Briefly, 1.35 g (0.01 mol) of p-aminobenzoic acid was dissolved in 14 ml of water and 3 ml of concentrated HCl. The mixture was cooled in an ice water bath until precipitates appeared. The precipitates disappeared after slow addition of sodium nitrite solution. The sodium nitrite solution was prepared by dissolving 0.752 g (0.011 mol) of sodium nitrite in 4 ml of water. The solution was vacuum filtered and then 1.465 g (0.013 mol) of sodium tetrafluoroborate was added. Then the solution was cooled below 0° C. to obtain white crystals, which were then vacuum filtered and washed with ice-cold ether and water. The diazonium salt was dried and then stored at 4° C.

Some embodiments include protein synthesis and purification for attached to $MoS_2$. In some embodiments, the GFP expression plasmid was constructed following previously described methods using the GFP variant GFPmut3b, and described in Green, Alexander A., Silver, Pamela A., Collins, James J. & Yin, P. Toehold Switches: De-Novo-Designed Regulators of Gene Expression. Cell 159, 925-939 (2014), the entire contents of which is incorporated by reference. The GFP gene was inserted into the pET15b (EMD Millipore) expression vector downstream of a T7 promoter and the polyhistidine tag sequence, yielding an N-terminal his-tagged GFP; and upstream of the T7 transcriptional terminator. The resulting plasmid was transformed into E. coli BL21 Star DE3. The transformed cells were cultured in 1 ml of LB medium with ampicillin (100 µg/ml) shaking at 37° C. in an incubator overnight. The overnight culture was diluted 1:600 with fresh LB medium containing ampicillin (50 µg/ml) and grown until its absorbance at 600 nm reached 0.6-0.8. IPTG was added into the culture to a final concentration of 0.5 mM to induce expression of T7 RNA polymerase and in turn trigger GFP production. After 4 hours of induction, the cells were harvested by centrifugation at 4000 g for 15 minutes. The cell pellet was resuspended in 27 ml lysis buffer (60 µg/ml lysozyme, 3.7 mM $NaH_2PO_4$, 16.3 mM $Na_2HPO_4$, 50 mM NaCl, 10 mM imidazole, 0.1 Protease Inhibitor Cocktail Tablet/ml) and sonicated at 4 W using a microtip probe (Branson Digital Sonifier 450D, 3 mm diameter tip). Three hundred 2-second pulses with a 2-second off time between each pulse were performed in an ice bath. The lysate was then centrifuged at 12,000 g for 30 min at 4° C. Approximately 25 ml of supernatant was collected and filtered through a 0.22-µm membrane filter. Purification was performed using fast protein liquid chromatography (FPLC) with a HisTrap HP column. After equilibrating the column using 100% Buffer A (3.7 mM $NaH_2PO_4$, 16.3 mM $Na_2HPO_4$, 500 mM NaCl, 20 mM imidazole, 0.3 mM TCEP, pH 7.5), 10 mL cleared lysate was loaded into the column, washed with 10% of Buffer B (3.7 mM $NaH_2PO_4$, 16.3 mM $Na_2HPO_4$, 350 mM NaCl, 500 mM imidazole, 0.3 mM TCEP, pH 7.5) and 90% of Buffer A, and eluted with 50% of Buffer B and Buffer A. Fractions were collected by monitoring the absorbance at 280 nm for the peak in its profile associated with the purified protein. Purified fractions collected from three FPLC runs were concentrated using Amicon (10 kD cutoff filters) and then stored in 50 mM $NaH_2PO_4$, 300 mM NaCl, pH 8.3. For smaller protein preparations, Ni-NTA spin columns (Qiagen) were used for purifying the His-tagged proteins. mCherry plasmid and protein preparation were performed using the same procedures as those used for GFP.

Some embodiments include protein attachment. In some embodiments, the protocols used for protein attachment were similar to previous reports of protein attachment to grapheme, and described in Wang, Q. H. et al. Understanding and controlling the substrate effect on graphene electron-transfer chemistry via reactivity imprint lithography. Nature Chem. 4, 724-732 (2012), and Lu, Y. et al. Graphene-protein bioelectronic devices with wavelength-dependent photoresponse. Appl. Phys. Lett. 100, 033110 (2012), the entire contents of which are incorporated by reference. In some embodiments, $MoS_2$ flakes exfoliated onto $SiO_2$/Si wafers were immersed in a 10 mM solution of 4-CBD and heated to 53-55° C. for 2 hours. The sample was washed with water, acetone, IPA and water again respectively, and after drying, immersed in a solution of 2 mM EDC and 5 mM sulfo-NHS solution prepared in 2-(N-morpholino)ethanesulfonic acid (MES) buffer (0.1 M MES sodium salt, 0.5 M NaCl, pH adjusted to 6 with 1.0 N HCl) for 20 min. The sample was rinsed with water and immediately immersed into 11.3 mM solution of $N_\alpha,N_\alpha$-Bis(carboxymethyl)-L-lysine hydrate (NTA-$NH_2$) prepared in 1×PBS for 2 hr. The wafer was washed with water and dipped in 11.3 mM solution of $NiCl_2$ for 40 min. The wafer was again rinsed with water and immersed in 8 µM solution of His-tagged EGFP (enhanced green fluorescent protein) for 1 hour and rinsed with water twice and then air dried. Confocal fluorescence microscope images were collected with a Leica TCS SP5 Spectral Confocal System using lasers with 488 nm and 561 nm wavelengths.

Figure 1B:
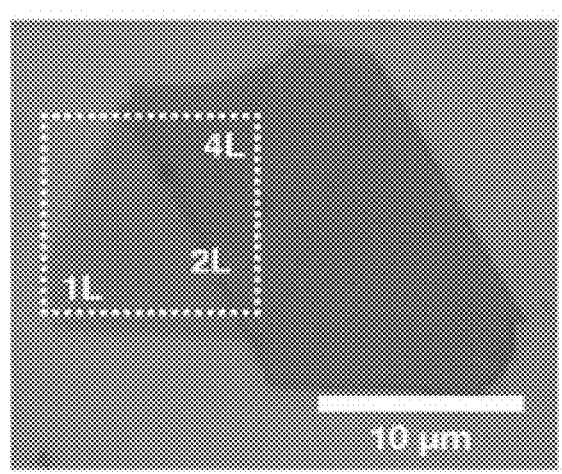
FIG. 1B illustrates an optical microscope image of a $MoS_2$ flake with monolayer (1L), bilayer (2L), and four-layer (4L) regions on a $SiO_2$/Si substrate in accordance with some embodiments of the invention.
Figure 1C:
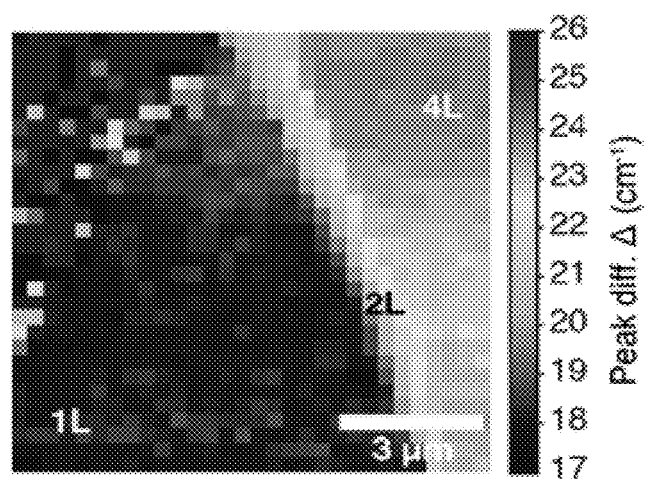
FIG. 1C illustrates a spatial map of the peak position difference between the out-of-plane $A_{1g}$ and in-plane $E^1_{2g}$ Raman peaks, $\Delta$, in accordance with some embodiments of the invention.
Figure 1D:
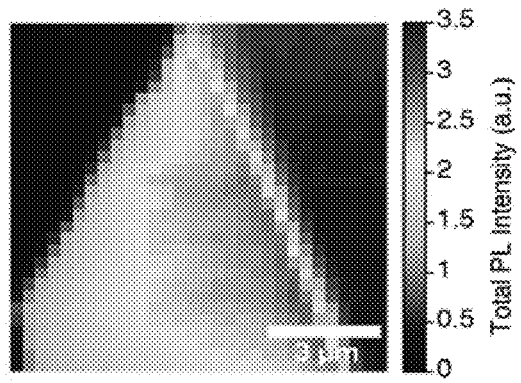
FIG. 1D shows a spatial map of the photoluminescence (PL) intensity in accordance with some embodiments of the invention.
Figures 1E, 1F:
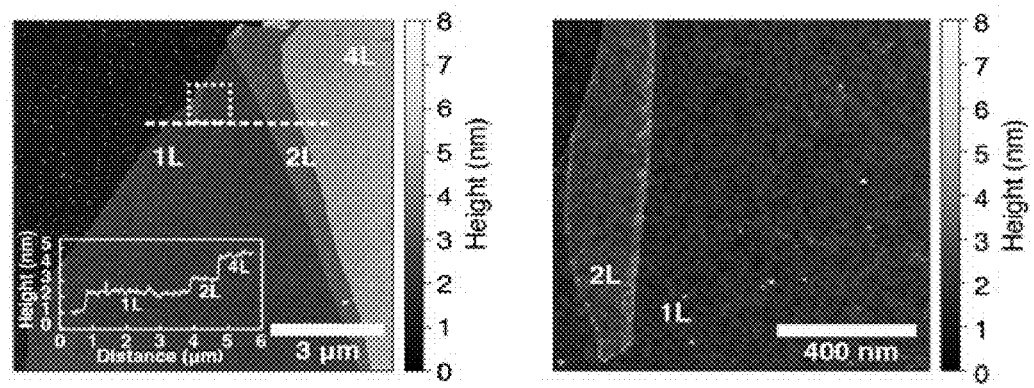
FIG. 1E shows an AFM image of the sample is shown in FIG. 1D in accordance with some embodiments of the invention.
FIG. 1F shows an AFM image that shows a region marked by the dashed square where there is mainly 1L with a smaller 2L region in accordance with some embodiments of the invention.
Figure 1G:
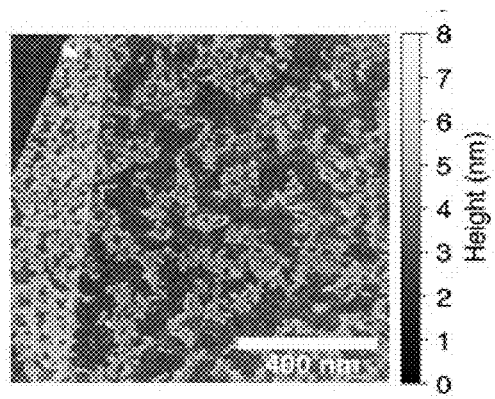
FIG. 1G shows numerous protrusions on the $MoS_2$ surface in accordance with some embodiments of the invention.

An optical microscope image of a MoS$_2$ flake with monolayer (1L), bilayer (2L), and four-layer (4L) regions on a SiO$_2$/Si substrate is shown in FIG. 1B. Raman spectroscopy and AFM imaging were used to identify the layer numbers. The corresponding spatial map (FIG. 1C) of the peak position difference between the out-of-plane A1g and in-plane E12g Raman peaks, Δ, which is a characteristic metric for identifying the number of MoS$_2$ layers, shows clear differences between the 1L, 2L, and 4L regions. A spatial map of the photoluminescence (PL) intensity is shown in FIG. 1D, also showing the increased PL from monolayer MoS$_2$ due to its direct bandgap. Further analysis of the PL of MoS$_2$ as a result of chemical functionalization is discussed below in FIG. 3. An AFM image of the sample is shown in FIG. 1D, and the height profile along the dashed line is shown in the inset. The region marked by the dashed square is shown in the AFM image of FIG. 1E, where there is mainly 1L with a smaller 2L region. After 5 s of reaction with 4-NBD, FIG. 1G shows numerous protrusions on the MoS$_2$ surface, which can be attributed to covalently attached nitrophenyl groups.

Figures 2A, 2B, 2C, 2D:
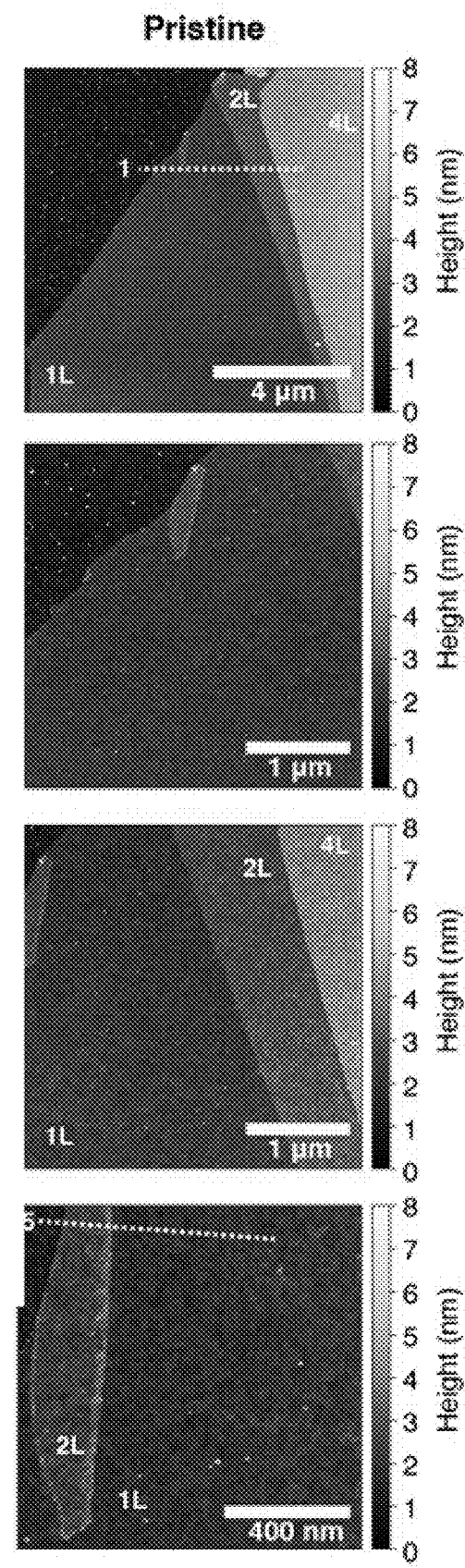
FIGS. 2A-2P include AFM imaging of organic groups on the $MoS_2$ surface as a function of reaction times with 4-NBD in accordance with some embodiments of the invention.
Figures 2E, 2F, 2G, 2H:
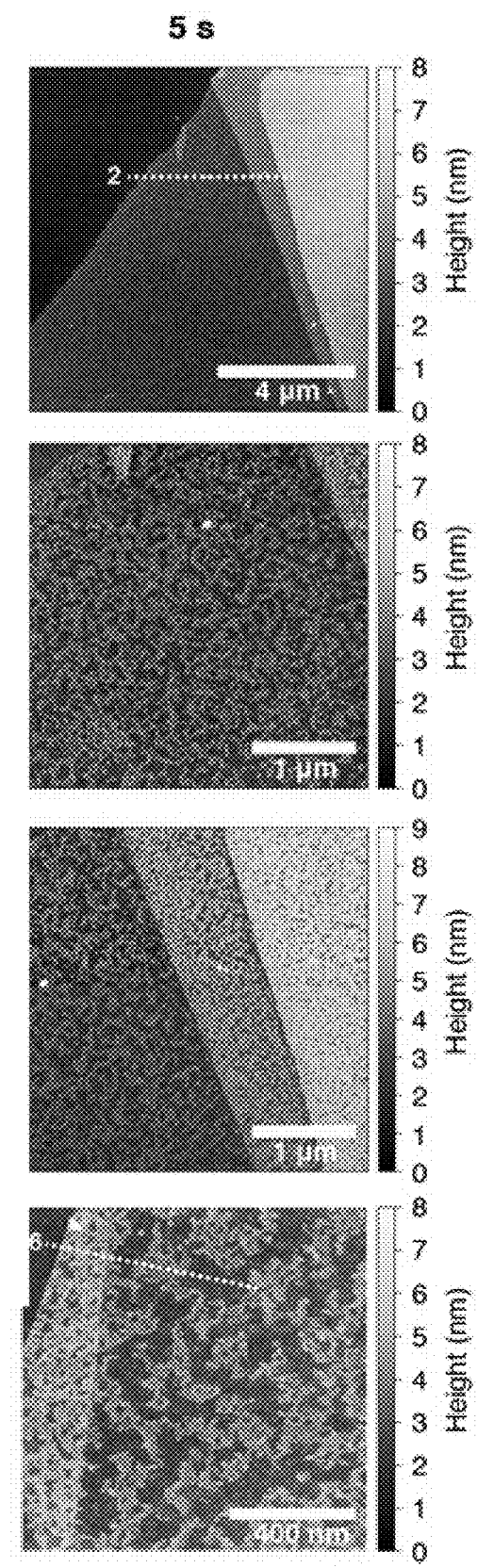
FIGS. 2Q-2R show height profile data of AFM images in accordance with some embodiments of the invention.
Figures 2I, 2J, 2K, 2L:
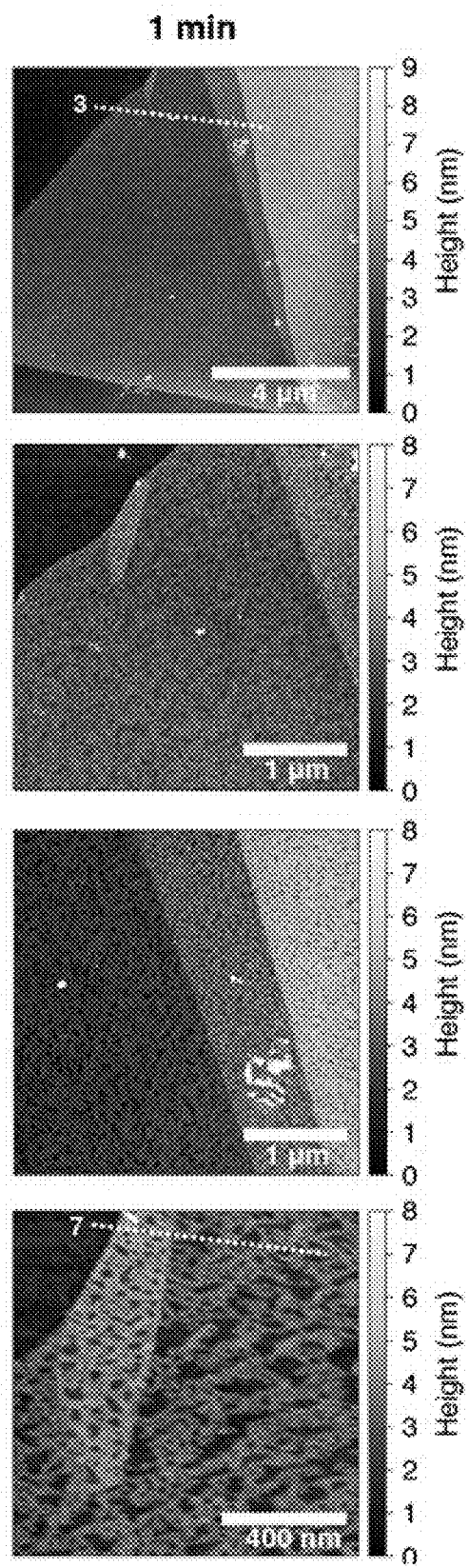
Figure 2M:
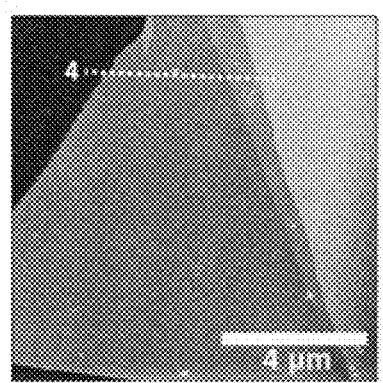
Figure 2N:
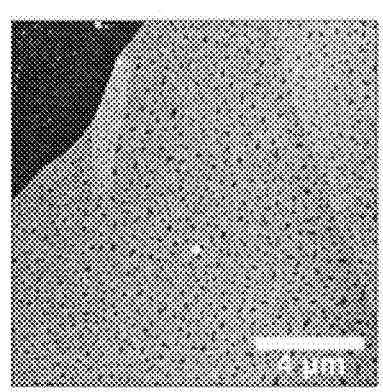
Figure 2O:
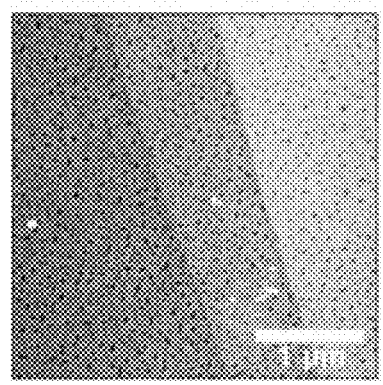
Figure 2P:
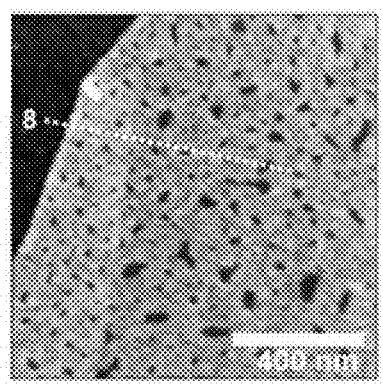
Figure 2Q:
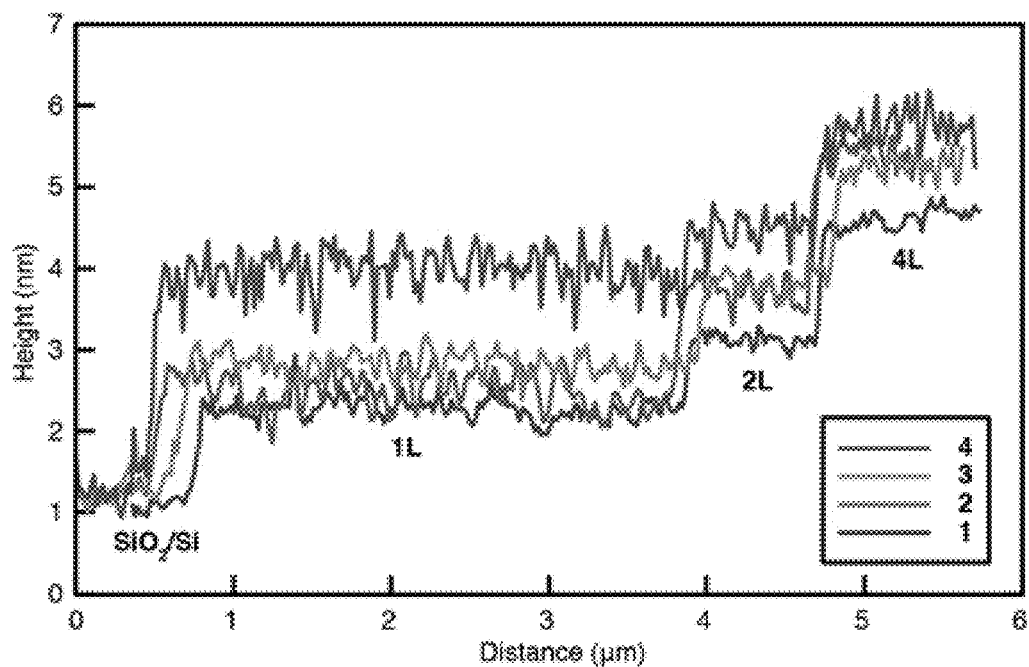
Figure 2R:
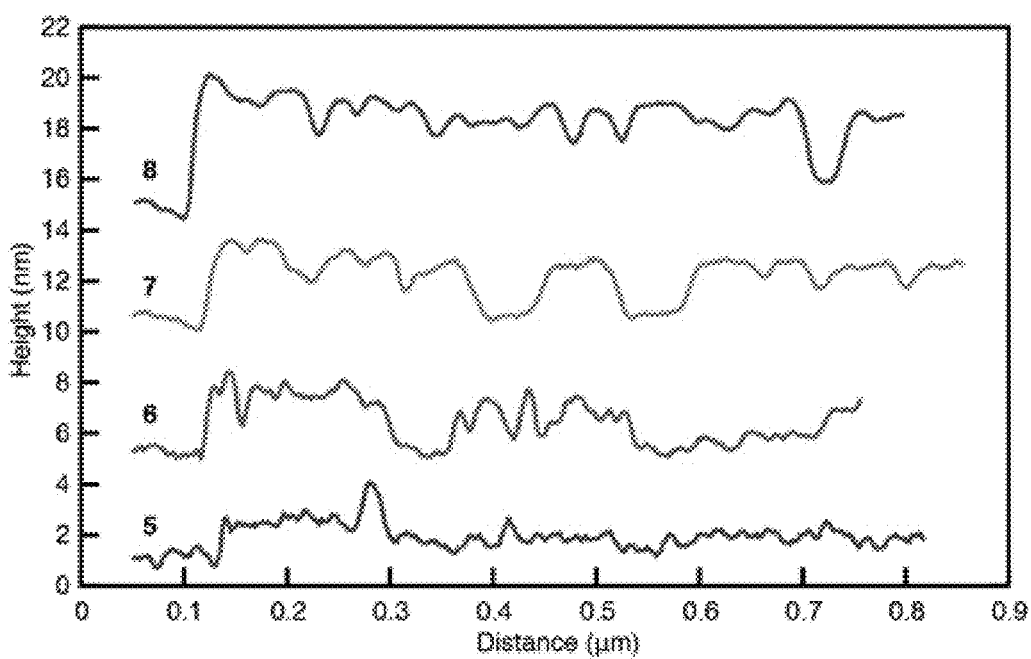
Figure 3A:
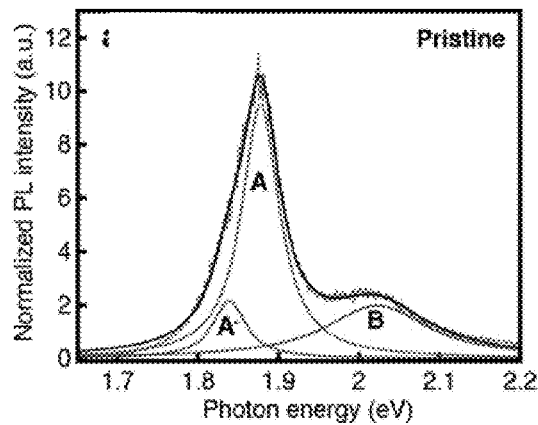
FIG. 3A-D shows changes in photoluminescence (PL) with reaction time in accordance with some embodiments of the invention.
Figure 3B:
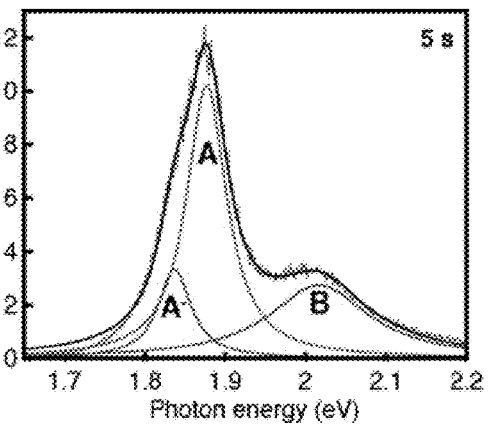
Figure 3C:
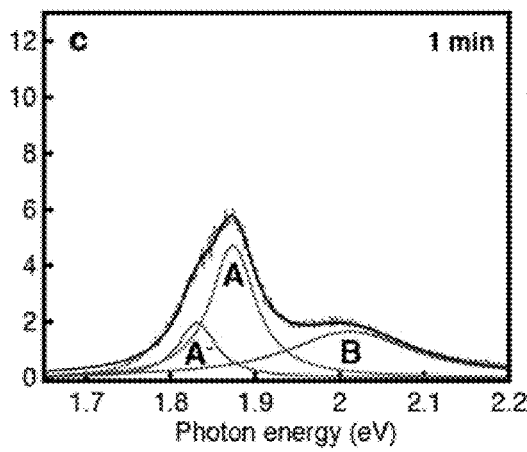
Figure 3D:
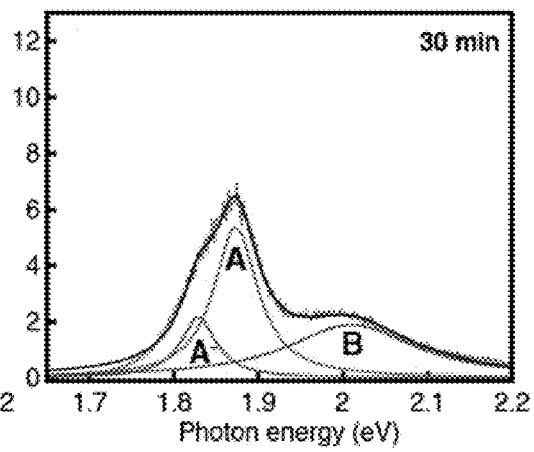
Figure 3I:
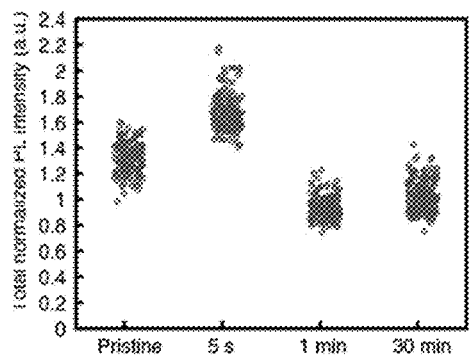
FIGS. 3I-3M show scatter plots of PL peak parameters for monolayer $MoS_2$ as a function of reaction time in accordance with some embodiments of the invention.
Figure 3J:
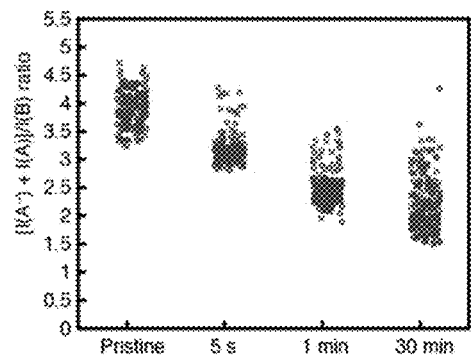
Figure 3K:
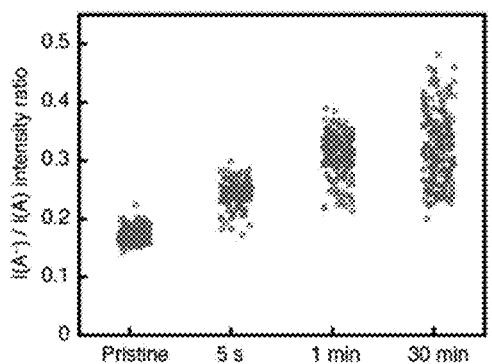
Figure 3L:
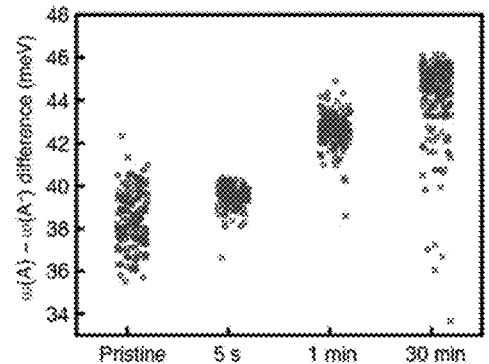
Figure 3M:
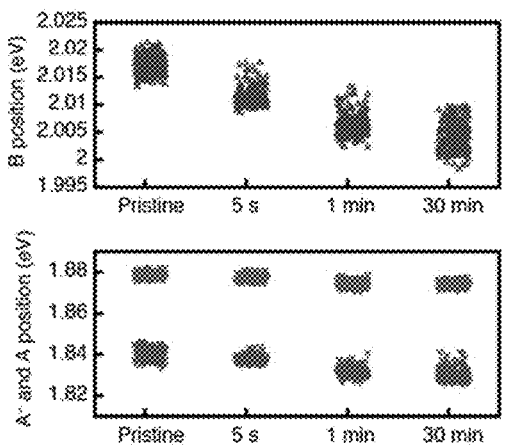

FIGS. 2A-2P include AFM imaging of organic groups on the MoS$_2$ surface as a function of reaction times with 4-NBD in accordance with some embodiments of the invention, and FIGS. 2Q-2R show height profile data of AFM images in accordance with some embodiments of the invention. The increasing coverage of organic groups on the MoS$_2$ surface as a function of reaction times with 4-NBD is revealed by AFM imaging in FIGS. 2A-2P. The bright protrusions in these images are interpreted as covalently bound nitrophenyl groups, although we cannot state with certainty whether each individual protrusion is one or more groups. The images show the same 1L, 2L, and 4L regions of the sample described earlier (FIG. 1B) in their pristine state, and after 5 seconds, 1 minute, and 30 minutes of reaction. The same sample was returned to the 4-NBD solution for increasing functionalization times and after each reaction step was characterized by AFM imaging and Raman and PL spectroscopy. Each row of images shows the same region of the sample, with increasing magnification in each subsequent row. The height profiles along the lines numbered 1-4 are shown in FIG. 2Q, and the lines numbered 5-8 are in FIG. 2R. At 5 seconds of reaction time (FIGS. 2E-2H), small chain-like protrusions can be observed across the MoS$_2$ surface, with a higher density of coverage for the thicker regions of the sample. There are no protrusions on the surrounding SiO$_2$ substrate. At 1 minute reaction time (FIGS. 2I-2L), the density of protrusions is higher, and the regions of unreacted MoS$_2$ is smaller. The initial chain-like clusters appear to have grown larger, rather than nucleating new clusters. By 30 minutes reaction time (FIGS. 2M-2P), the reacted groups are even more densely covering the MoS$_2$, and the remaining unreacted areas of MoS$_2$ form small pores. In some embodiments, on the thicker MoS$_2$ regions, a higher density of attached groups is observed. This effect is most clearly visible in the third and fourth rows of AFM images in FIGS. 2C-2D, 2G-2H, 2K-2I, and 2O-2P. At the shorter reaction times, there are more clusters and they are closer together in the 2L and 4L regions than in the 1L region, while at the longer reaction times the remaining pinholes in the 2L and 4L regions are smaller than in the 1L region.

Photoluminescence (PL) of MoS$_2$ as a function of increasing diazonium functionalization and related characterization data is show and discussed in FIGS. 3A-3M. For example, FIG. 3A-D shows changes in photoluminescence (PL) with reaction time in accordance with some embodiments of the invention, and FIGS. 3E-3H show raman peaks with spatial maps as a function of reaction time in accordance with some embodiments of the invention. FIGS. 3I-3M show scatter plots of PL peak parameters for monolayer MoS$_2$ as a function of reaction time in accordance with some embodiments of the invention. MoS$_2$ exhibits PL due to recombination of excitons and trions (negatively charged excitons). There are three main PL peaks identified for MoS$_2$: the A and B peaks due to excitons at the direct band gap with spin orbit splitting in the valence band at about 1.86 eV and 2.0 eV, respectively, and the A$^-$ peak due to trions (negatively charged excitons) at about 1.82 eV. Representative PL spectra of pristine monolayer MoS$_2$ and after 4-NBD functionalization for 5 seconds, 1 minute, and 10 minutes are shown in FIGS. 3A-3D along with Lorentzian fits to deconvolute each of the A$^-$, A, and B peaks. The spectra are normalized to the intensity of the Raman peaks to account for the increased material in thicker layers and to remove the effect of small changes in laser power between experiments. The individual spectra in FIGS. 3A-3D come from PL spectral maps covering a 10 μm×10 μm area. The total integrated intensity of the PL peaks are shown in the spatial maps in FIGS. 3E-3H, which feature the same region of the sample as previously shown. In the PL intensity map for pristine MoS$_2$, FIG. 3E, we observe that the intensity is clearly much higher in the 1L region than the 2L and 4L regions due to the direct bandgap of 1L MoS$_2$. Throughout the aryl diazonium covalent functionalization process, the PL emission is maintained at energies that are close to the initial values, indicating that the electronic structure of the semiconducting MoS$_2$ is intact. The PL spectra change in their intensities and constituent peak parameters as the diazonium functionalization time increases. To convey these changes, scatter plots of different peak parameters from across the monolayer MoS$_2$ region illustrate the trends with reaction time. The overall PL intensity is observed to slightly increase at 5 seconds reaction, visible in both the individual spectra and scatter plots in FIG. 3I, where the total integrated PL intensity is plotted as a function of diazonium reaction time. The intensity then decreases at 1 minutes and 10 minute to levels slightly below the initial level. We note that there is a distribution of values in these scatter plots, showing that there is spatial variation in the samples and that spatial mapping of PL emission rather than individual spectra at isolated locations is important to gain a more complete understanding. The change in overall PL intensity is related to the intensities of the A$^-$ and A peaks relative to the B peak, which is plotted as [I(A$^-$)+I(A)]/I(B) in FIG. 3J. This ratio decreases with reaction time. The A peak becomes smaller than the A$^-$ peak, as shown in the decrease of the I(A$^-$)/I(A) ratio with reaction time in FIG. 3K. The position difference between the A$^-$ and A peaks, ω(A)−ω(A$^-$), increases with reaction time in FIG. 3L. Finally, the positions of each peak shifts to lower energies with reaction time in FIG. 3M, with the B peak shifting more than the A and A$^-$ peaks.

These changes described above can be interpreted as being primarily due to doping. Changes to the exciton (A peak) and trion (A$^-$ peak) photoluminescence in MoS$_2$ as a function of doping level from neutral to highly n-doped have been reported by others. In particular, the difference in exciton and trion energies, ω(A)−ω(A$^-$), was shown to correspond linearly to the Fermi energy as ω(A)−ω(A$^-$)= $E_{A-}+E_F$, where $E_{A-}$ is the trion binding energy of ~18 meV.

According to this relation, we estimate that our pristine samples with a median energy difference of ~38 meV corresponds to a Fermi energy of ~20 meV, and after 30 min of diazonium functionalization the median energy difference of ~45 meV corresponds to a Fermi energy of ~27 meV. This change suggests that the n-type pristine sample, which is consistent with previous reports of n-type behaviour in $MoS_2$, which becomes more n-doped with diazonium functionalization. It has been shown that the PL intensity of the $A^-$ trion peak remains relatively constant across doping levels, while while the relative intensity of the A exciton peak decreases for increasing n-doping. This observation of the relative change in A and $A^-$ peak intensities agrees with the data in FIG. 3K, which then also suggests increasing n-doping with functionalization. Decreases in this ratio have been measured for liquids of increasing dielectric constants surrounding $MoS_2$, suggesting there is a strong influence from changing effective dielectric constant as the nitrophenyl groups increasingly coat the $MoS_2$ surface. Shifting of the position of the $A^-$ trion PL peak toward lower energies with increasing n-doping observed by Mak et al. is also seen in our data with increasing functionalization in FIG. 3M. The n-doping in our 4-NBD functionalized samples can be attributed to the effect of the electron-donating $NO_2$ group. Finally, the total PL intensity shows changes with increasing functionalization.

Figure 4:
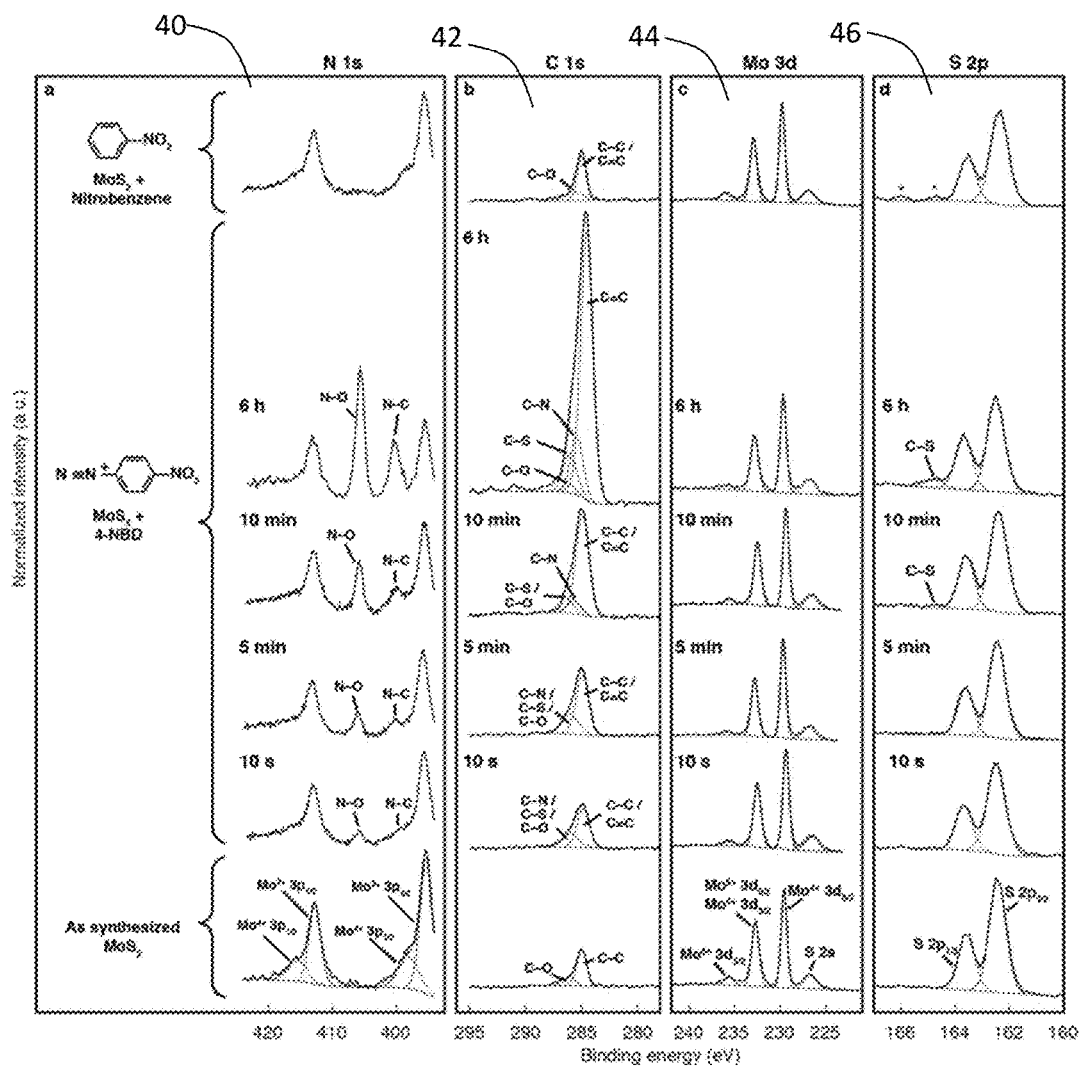
FIG. 4 shows XPS spectra for as-synthesized $MoS_2$ in accordance with some embodiments of the invention.

X-ray photoelectron spectroscopy (XPS) was used to characterize the chemical bonding occurring from diazonium functionalization. Large-area samples of $MoS_2$ grown by chemical vapor deposition (CVD) described earlier were used for these measurements rather than mechanically exfoliated flakes to accommodate the ~400 µm X-ray spot size. Several CVD-grown $MoS_2$ samples were functionalized by 4-NBD under the same reaction conditions as shown in the previous experiments for different reaction times: 10 seconds, 5 minutes, 10 minutes, and 6 hours. Control experiments were also conducted by immersing $MoS_2$ in concentrated nitrobenzene for 4 hours. The resulting XPS spectra are shown in FIG. 4 for as-synthesized $MoS_2$, for $MoS_2$ at different 4-NBD functionalization times, and for the nitrobenzene-exposed $MoS_2$ control sample. The spectra were normalized to the intensity of the Mo peak because the Mo atoms are sandwiched between S atoms in the $MoS_2$ structure and are not expected to participate in surface reactions. The black curves are the experimental data and the colored curves are peak fits. In the N 1s region (show as 40), two peaks are shown due to Mo 3p in the spectra for all the reaction conditions. With increasing 4-NBD functionalization time, peaks from N—O and N—C bonds arise and increase in intensity. These peaks are due to the $NO_2$ group in the 4-NBD molecule being attached to the $MoS_2$ surface. However, the nitrobenzene control sample shows no N peak, even though high concentrations of nitrobenzene were in contact with the $MoS_2$ for 4 h, indicating that no covalent bonds to the surface have formed, and no significant N-containing groups are on the surface. The 10 s diazonium functionalized sample has a much larger N—O peak. In the C is region (shown as 42), there is a small peak associated with adventitious carbon from atmospheric hydrocarbons for the as-synthesized $MoS_2$. With increasing 4-NBD functionalization time, the C peak attributed to aromatic C=C bonds, C—N bonds from the nitrophenyl groups covalently attached to the $MoS_2$ surface, and C—S bonds at the functionalization sites increase in intensity and becomes quite large for the longest reaction time with the main contribution coming from C=C. In the spectrum for the nitrobenzene control, the C peak is similar in size to the initial adventitious carbon peak from unfunctionalized $MoS_2$, and perhaps slightly larger due to some residual physisorption of molecules. This is again consistent with no covalent bonding to the $MoS_2$ surface when the diazonium group is absent. In the Mo 3d region (shown as 44), there are typical peaks associated with the Mo and S that occurs in $MoS_2$, as well as some small Mo peaks associated with residual $MoO_3$ precursor from the CVD process that has not been fully sulfurized. After functionalization, there are no significant changes to the Mo peaks, consistent with the Mo atoms sandwiched between the S atoms in the $MoS_2$ structure and not participating in any surface reactions. In the S 2p region (shown as 46), the two characteristic S peaks due to spin-orbit splitting can be observed. With 4-NBD functionalization, a new peak associated with C—S bonds appears, suggesting the successful formation of covalent bonds between the C atoms in aryl groups and the S atoms at the top surface of $MoS_2$. This peak is relatively small, even for the 6 hour diazonium functionalized sample, because not all surface atoms are reacted due to steric hindrance and kinetic barriers, and because the samples are multilayer, so there is a larger contribution from the unreacted S. From additional thermogravimetric analysis (TGA) measurements discussed below, it is estimated that there is about 12% coverage of covalently reacted sites on the $MoS_2$ surface. Another possible factor is that some of the 4-NBD groups may be attaching to existing covalently bound groups to form oligomers rather than to the bare $MoS_2$ surface, so that the number of C—S bonds does not increase in proportion to the overall amount of additional N and C on the surface with increasing reaction time. Similar oligomer formation was reported for aryl diazonium functionalization of graphene.

In the nitrobenzene control sample, the two small peaks marked by (*) are likely due to Na contamination from the soda lime glass pipettes used to transfer nitrobenzene from its container to the sample, and thus forming sodium sulfate, rather than from C—S bonds. All other labware used in these experiments, including for the diazonium reaction, was either plastic or borosilicate glass that did not add any further XPS peaks. Wide scan XPS spectra for as-synthesized $MoS_2$, after 4-NBD functionalization 6 h, and after nitrobenzene exposure for 4 h showed that no B or F peaks were visible, indicating that the $BF_4^-$ counterion was fully removed during the rinsing steps.

Figure 5A:
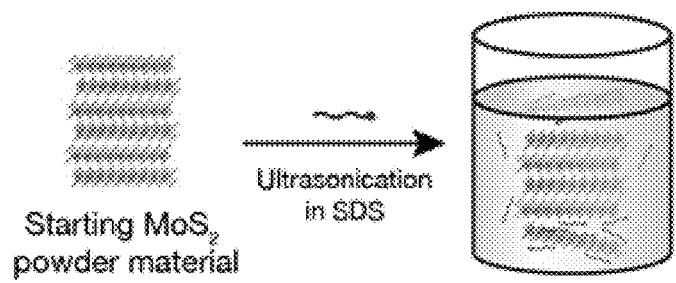
FIG. 5A shows the process of dispersion and functionalization of pristine bulk $MoS_2$ dispersed in a surfactant solution in accordance with some embodiments of the invention.
Figure 5B:
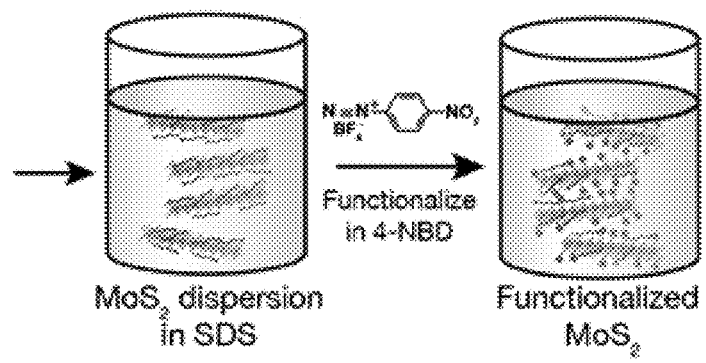
FIG. 5B shows a photograph of the dispersion of $MoS_2$ in accordance with some embodiments of the invention.
Figure 5B:
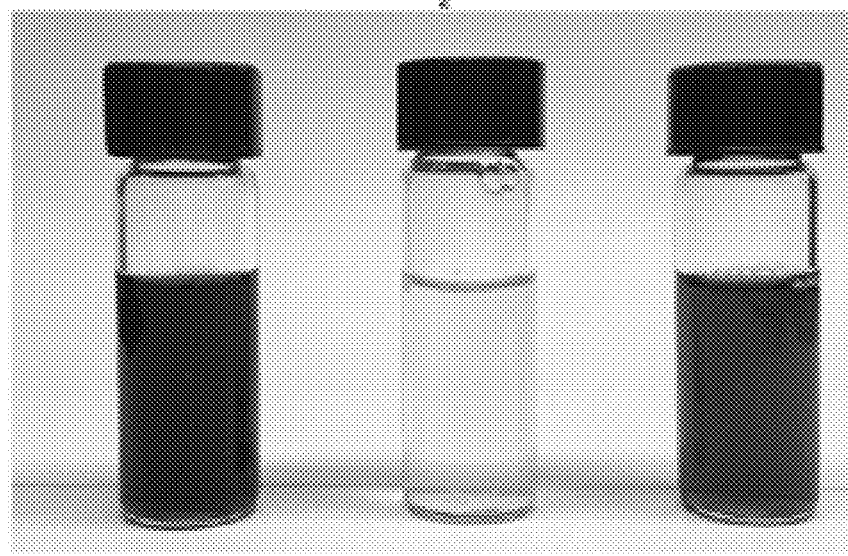
Figure 5C:
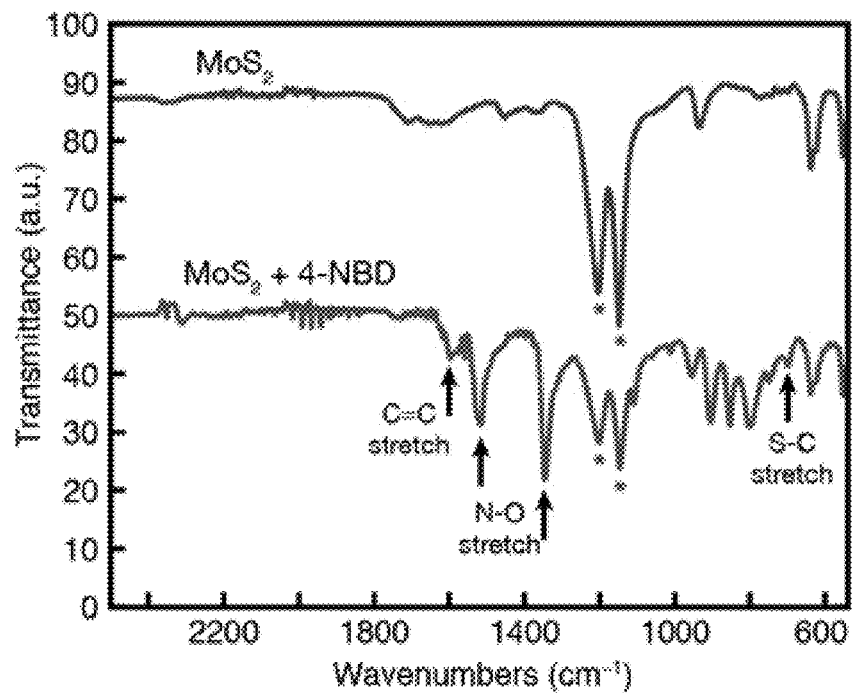
FIG. 5C shows an FTIR spectrum of diazonium-functionalized $MoS_2$ in accordance with some embodiments of the invention.
Figure 5D:
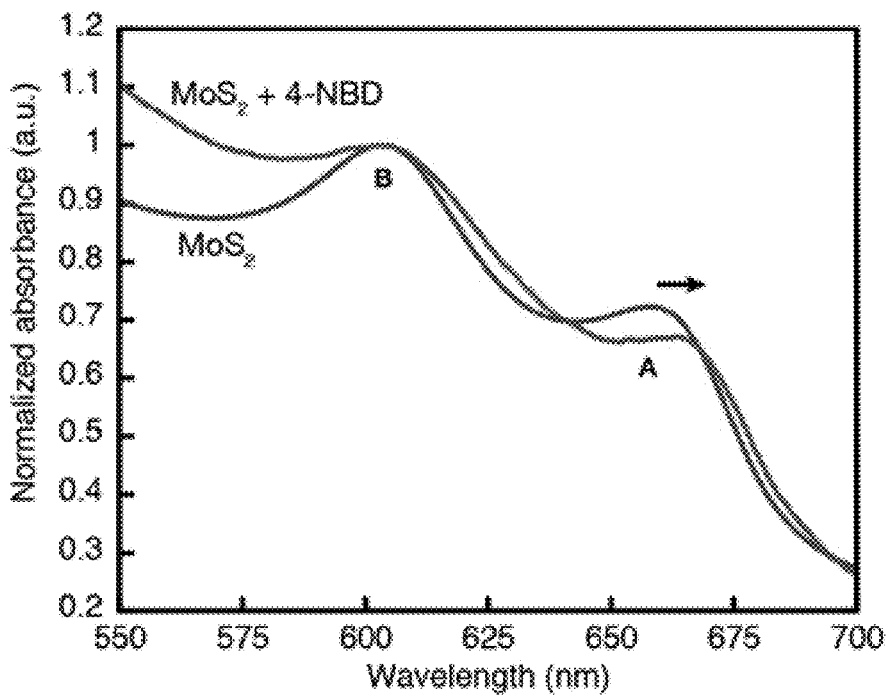
FIG. 5D shows an optical absorbance spectra (UV-vis) obtained for re-dispersed samples of $MoS_2$ in accordance with some embodiments of the invention.
Figure 5E:
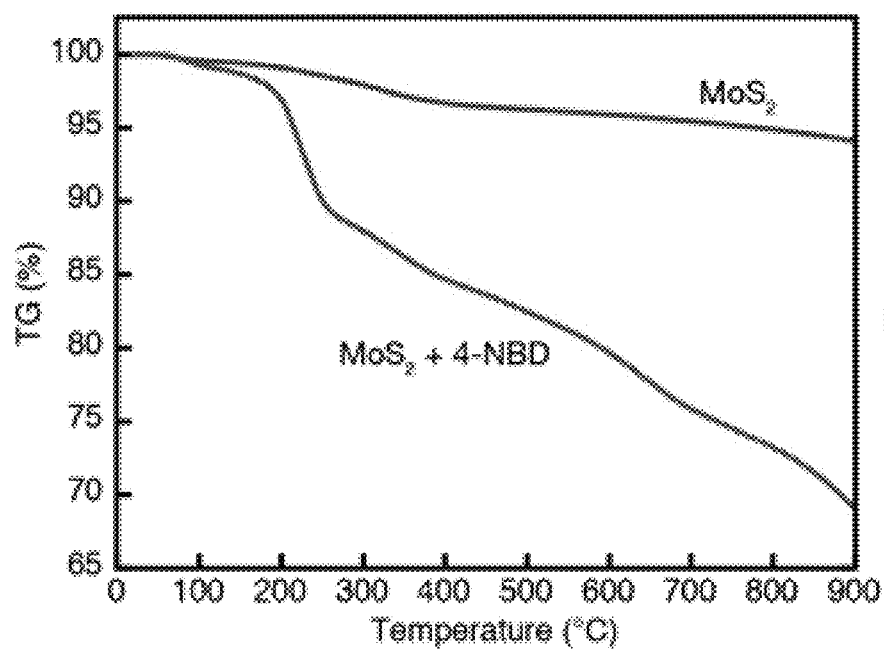
FIG. 5E shows a thermogravimetric analysis (TGA) mass loss curve for $MoS_2$ (green curve) and 4-NBD functionalized $MoS_2$ in accordance with some embodiments of the invention.
Figure 5F:
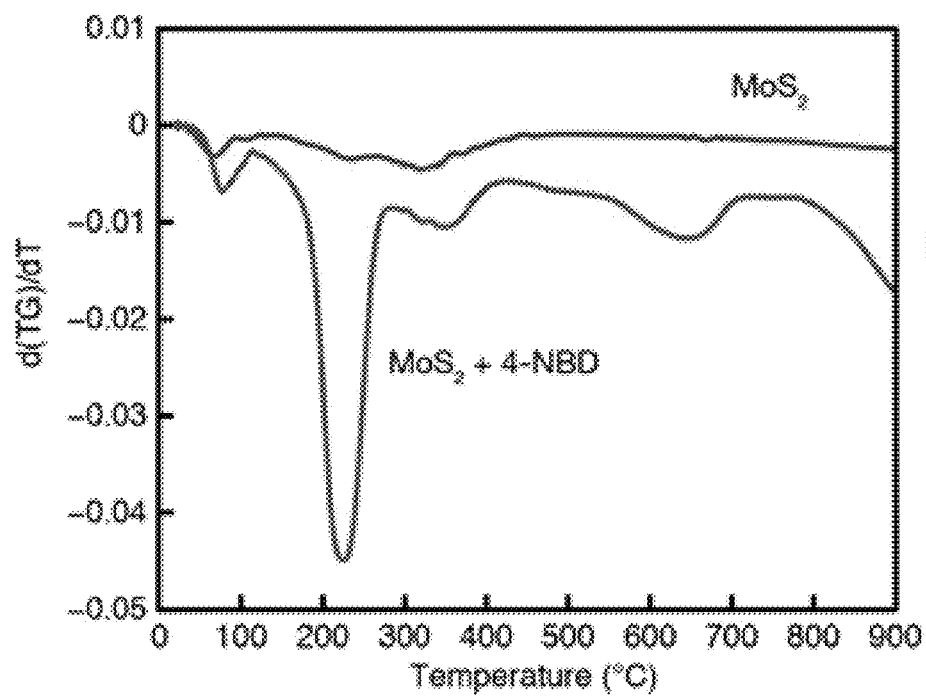
FIG. 5F is a TGA derivative (DTG) curves for the mass loss curves in FIG. 5E, showing dips corresponding to key mass loss components in accordance with some embodiments of the invention.

In some embodiments, pristine bulk $MoS_2$ dispersed in a surfactant solution was functionalized where diazonium-functionalized $MoS_2$ was shown to be stable in aqueous dispersions. FIG. 5A shows the process of dispersion and functionalization of pristine bulk $MoS_2$ dispersed in a surfactant solution in accordance with some embodiments of the invention, and FIG. 5B shows a photograph of the dispersion of $MoS_2$ in accordance with some embodiments of the invention. FIG. 5C shows an FTIR spectrum of diazonium-functionalized $MoS_2$ in accordance with some embodiments of the invention, and FIG. 5D shows an optical absorbance spectra (UV-vis) obtained for re-dispersed samples of $MoS_2$ in accordance with some embodiments of the invention. FIG. 5E shows a thermogravimetric analysis (TGA) mass loss curve for $MoS_2$ (green curve) and 4-NBD functionalized $MoS_2$ in accordance with some embodiments of the invention, and FIG. 5F is a TGA derivative (DTG) curves for the mass loss curves in FIG. 5E, showing dips corresponding to key mass loss components in accordance with some embodiments of the invention. To prepare the initial dispersion, $MoS_2$ was probe-sonicated in an aqueous solution of sodium dodecyl sulfate (SDS) solution to shear the sheets apart, which were then stabilized by the SDS molecules. A photograph of this dispersion is shown in FIG. 5B. In some embodiments, to functionalize this solution-dispersed $MoS_2$, 100 mg of 4-NBD was added and it was again probe-sonicated to allow the salt to react. Sonication helped in producing more accessible sites for the diazonium salt to react allowing efficient functionalization. To remove excess 4-NBD, and any side products that may have formed (such as nitrobenzene from the dissociation of the diazo salt), the resulting dispersion was flocculated with ethanol, filtered over an Omnipore filter membrane (100 nm pore size) and washed thoroughly with water and ethanol. The $MoS_2$ films collected on the filter membranes were characterized by Fourier transform infrared (FTIR) spectroscopy. In FIG. 5C, the FTIR spectrum of diazonium-functionalized $MoS_2$ clearly shows the presence of characteristic peaks that confirmed successful covalent modification $MoS_2$ in bulk dispersions. The peaks at ~1518 $cm^{-1}$ and ~1344 $cm^{-1}$ represent the stretching vibrations of the N—O bond in the $NO_2$ group, the peak at 1595 $cm^{-1}$ represents C=C stretching vibrations in the aromatic ring, and the peak at 697 $cm^{-1}$ can be assigned to S—C stretching vibrations at the covalent bond between the $MoS_2$ surface. After acquiring the FTIR spectra, the films were re-dispersed in a fresh SDS solution using bath sonication. The diazonium-functionalized $MoS_2$ material provided a highly concentrated dispersion after bath sonication in contrast to un-functionalized $MoS_2$, which was only weakly re-dispersed. Photographs of the re-dispersed samples are shown in FIG. 5B. This change in dispersibility can be attributed to a change in surface energy, a phenomenon which has been previously reported for dispersions of TMDCs, and for covalently functionalized graphene. Optical absorbance spectra (UV-vis) were obtained for the re-dispersed samples as shown in FIG. 5D. The peaks at ~605 nm and ~660 nm are attributed to the B and A excitonic transitions, respectively. After functionalization, the B peak positions remains the same while the A peak shifts toward longer wavelengths. The redshift can be attributed to electronic coupling of excitons to the conjugated aromatic groups attached to the $MoS_2$ surfaces. The increase in absorbance for functionalized $MoS_2$ below ~575 nm is attributed to absorbance of the attached organic groups.

Further characterization of the bulk $MoS_2$ dispersions with and without diazonium functionalization was conducted using thermogravimetric analysis (TGA) under helium atmosphere. The TGA curves and first derivative curves are shown in FIGS. 5E-5F. The first derivative curve contains dips that more clearly indicate the temperatures of transitions or sharp changes in mass loss. The functionalized and un-functionalized $MoS_2$ both show a small mass loss below 100° C., which may be due to residual adsorbed water and other small molecules. There is also some mass loss below 200° C., which is more prominent for the functionalized $MoS_2$, that may be due to van der Waals bonded molecules. A sharp mass loss peak, corresponding to a mass loss of about 8%, occurs between 200° C. to 300° C., with the maximum loss rate occurring at about 225° C. This sharp mass loss peak suggests the breaking of covalent bonds for species attached to the $MoS_2$ surface and the loss of nitrophenyl groups from the surface. There is also continued mass loss above 300° C., but it occurs at a faster rate, and with an additional peak at ~650° C. and accelerating further above 800° C., which can be attributed to lattice degradation with at higher temperatures. Using the mass loss of the functionalized sample between 100° C. and 450° C., which is about 15.7%, and using the molar masses of nitrobenzene and $MoS_2$, surface coverage can be estimated to be about 24% assuming both sides of a monolayer $MoS_2$ flake in solution are available, or approximately 12% coverage on each side.

Figure 6A:
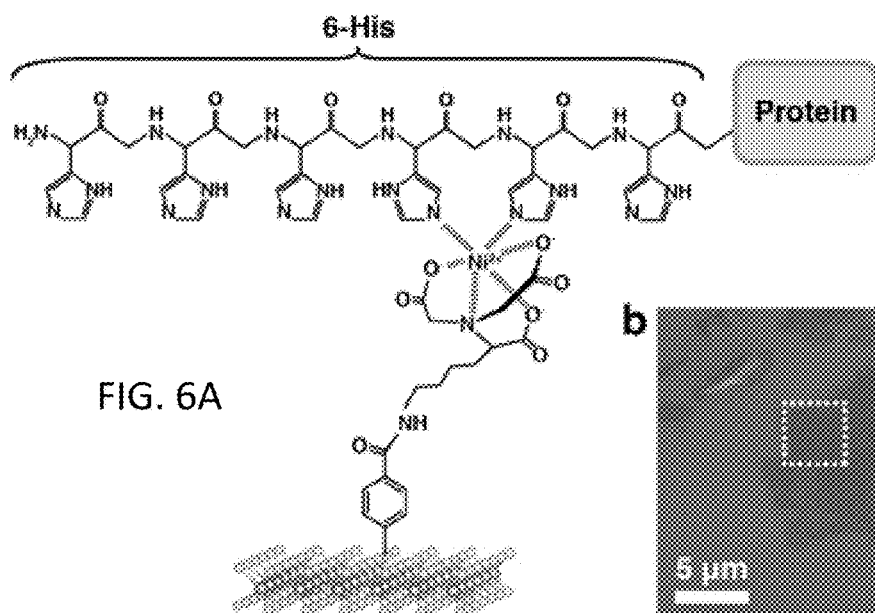
FIG. 6A shows attachment of proteins to $MoS_2$ with schematic of NTA-Ni-chelation attachment of poly-histidine (His) tagged protein, linked to $MoS_2$ surface via diazonium functionalization chemistry in accordance with some embodiments of the invention.
Figure 6B:
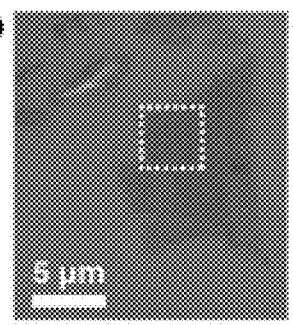
FIG. 6B shows an optical microscope image of mechanically exfoliated $MoS_2$ flakes featured in panels of FIGS. 6C-6D in accordance with some embodiments of the invention.
Figure 6C:
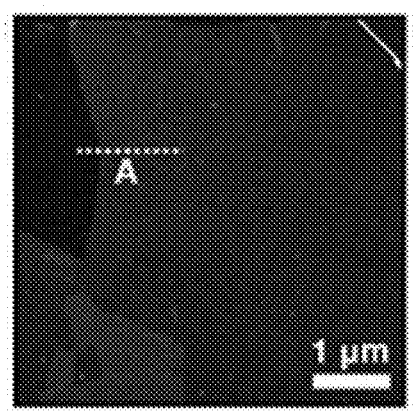
FIG. 6C shows an AFM image of pristine $MoS_2$ in the region indicated by the dashed square in panel of FIG. 6B in accordance with some embodiments of the invention.
Figure 6D:
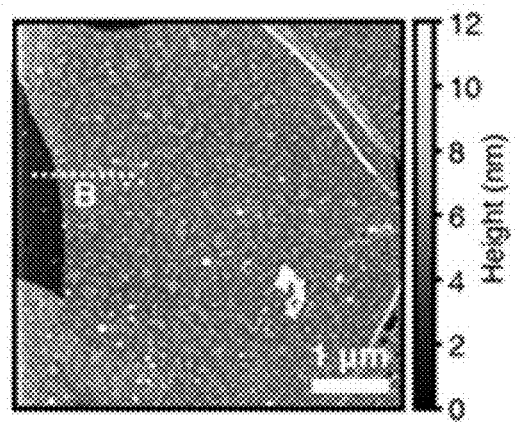
FIG. 6D shows an AFM image in the same region as panel of FIG. 6C after attachment of mCherry (red fluorescent protein) with initial 10 min functionalization with 4-CBD in accordance with some embodiments of the invention.
Figure 6E:
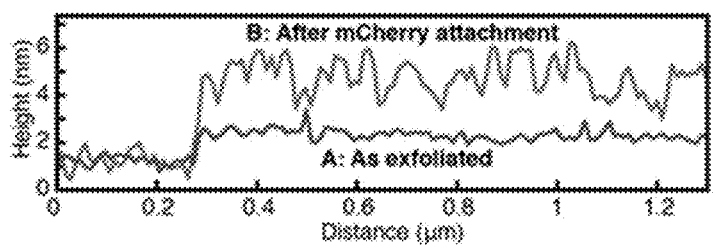
FIG. 6E shows height profiles along lines A and B of FIG. 6C-6D in accordance with some embodiments of the invention.
Figure 6F:
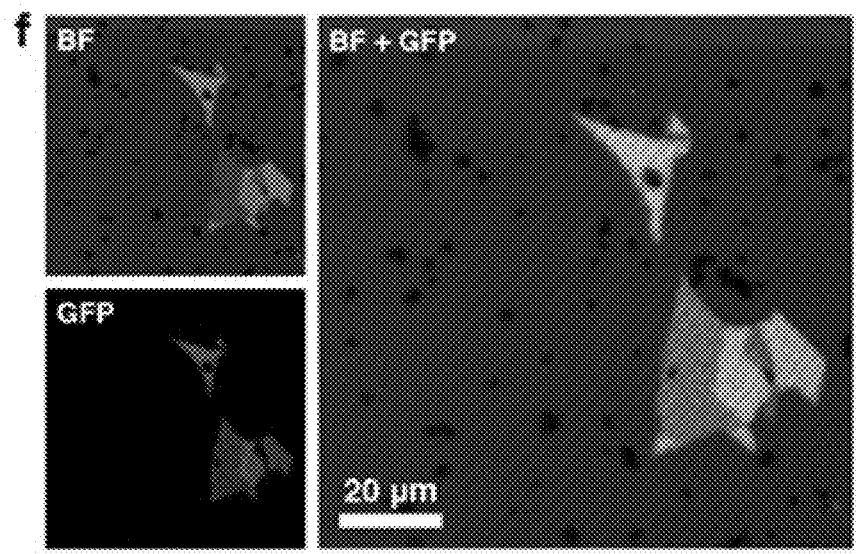
FIG. 6F shows GFP attachment in accordance with some embodiments of the invention.
Figure 6G:
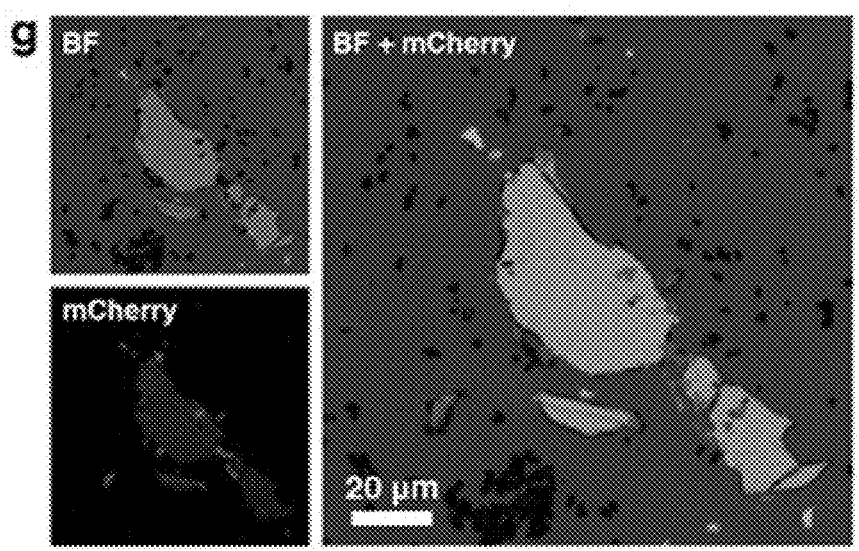
FIG. 6G shows mCherry attachment in accordance with some embodiments of the invention.
Figure 6H:
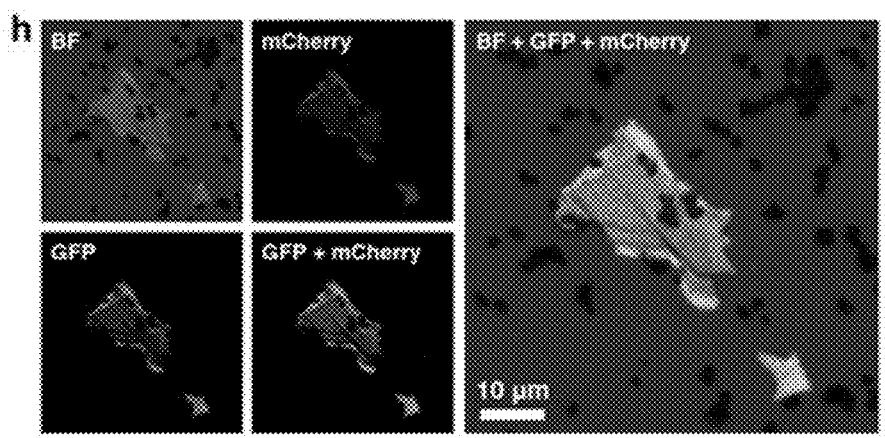
FIG. 6H shows 1:1 mixture of GFP and mCherry attachment in accordance with some embodiments of the invention.

Some embodiments include methods to tether fluorescent proteins to the $MoS_2$ surface. FIG. 6A shows attachment of proteins to $MoS_2$ with schematic of NTA-Ni-chelation attachment of poly-histidine (His) tagged protein, linked to $MoS_2$ surface via diazonium functionalization chemistry in accordance with some embodiments of the invention. Further, FIG. 6B shows an optical microscope image of mechanically exfoliated $MoS_2$ flakes featured in panels of FIGS. 6C-6D in accordance with some embodiments of the invention. FIG. 6C shows an AFM image of pristine $MoS_2$ in the region indicated by the dashed square in panel of FIG. 6B in accordance with some embodiments of the invention. Further, FIG. 6D shows an AFM image in the same region as panel of FIG. 6C after attachment of mCherry (red fluorescent protein) with initial 10 min functionalization with 4-CBD in accordance with some embodiments of the invention. FIG. 6E shows height profiles along lines A and B of FIG. 6C-6D in accordance with some embodiments of the invention. Further, FIG. 6F shows GFP attachment in accordance with some embodiments of the invention. FIG. 6G shows mCherry attachment in accordance with some embodiments of the invention, and FIG. 6H shows 1:1 mixture of GFP and mCherry attachment in accordance with some embodiments of the invention. In some embodiments, carboxylic acid groups were grafted to the $MoS_2$ surface using 4-carboxybenzenediazonium (4-CBD) tetrafluorobate functionalization (UV-vis spectra of bulk $MoS_2$ functionalized by 4-CBD. The 4-CBD functionalized $MoS_2$ was then subsequently reacted to allow tethering of poly-histidine (His)-tagged green fluorescent protein (GFP) and red fluorescent protein mCherry as described earlier, where the chemical attachment is schematically illustrated in FIG. 6A. Some embodiments included the use of mechanically exfoliated $MoS_2$, as shown in the optical microscope image of FIG. 6B. AFM imaging of the pristine $MoS_2$ shows smooth atomic steps (FIG. 6C). After the protein attachment steps, AFM imaging (FIG. 6D) shows a uniform increase in thickness (FIG. 6E) that can be interpreted as a layer of proteins attached via the Ni-chelating linkage shown in the schematic, along with some pinholes consistent with those observed for nitrobenzenediazonium attachment discussed earlier. To confirm attachment of active, viable proteins, confocal fluorescence microscopy was used to image the samples. FIGS. 6F-6G show bright field optical images along with fluorescent images in green and red channels for GFP and mCherry emission, respectively. These images indicate that actively fluorescing proteins have successfully been attached to the $MoS_2$ regions where the initial diazonium functionalization took place, and not in regions of the bare $SiO_2$/Si substrates. FIG. 6H shows the result of attaching a mixture of GFP and mCherry. The overlay of both red and green channels on the bright field image, resulting in a combined yellow appearance, shows that both proteins have been uniformly localized to the $MoS_2$ flakes.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent or publication cited herein is incorporated by reference, as if each such patent or publication were individually incorporated by reference herein. Various features and advantages of the invention are set forth in the following claims.

The invention claimed is:

1. A method comprising:
   providing at least one bulk transition metal dichalcogenide crystal;
   in the absence of chemical exfoliation, mechanically exfoliating the at least one bulk transition metal dichalcogenide crystal to produce
   at least one transition metal dichalcogenide with exfoliated surfaces of entirely semiconducting 2H phase;
   without first converting the semiconducting 2H phase to a metallic 1T phase by exposure to an alkyl lithium compound, reacting at least a portion of the semiconducting 2H phase of the at least one transition metal dichalcogenide with the at least one aryl diazonium salt by exposing at least a portion of the at least one transition metal dichalcogenide to at least one aryl diazonium salt in the absence of an alkyl lithium; and
   wherein the reaction of the at least one aryl diazonium salt with the at least one transition metal dichalcogenide occurs with the semiconducting 2H phase to produce at least one aryl diazonium functionalized transition metal dichalcogenide.

2. The method of claim 1, wherein the at least one aryl diazonium salt is 4-nitrobenzenediazonium tetrafluoroborate.

3. The method of claim 1, wherein the at least one aryl diazonium salt is 4-carboxybenzenediazonium tetrafluoroborate.

4. The method of claim 1, wherein the semiconducting 2H phase of the at least one transition metal dichalcogenide is derived directly using sonication of a solution of the at least one transition metal dichalcogenide.

5. The method of claim 1, wherein the at least one transition metal dichalcogenide is $MoS_2$.

6. The method of claim 5, wherein the $MoS_2$ reacts with the at least one aryl diazonium salt without prior conversion of the semiconducting 2H phase to metallic 1T phase.

7. The method of claim 1, wherein the at least one aryl diazonium salt comprises an aqueous solution of the aryl diazonium salt.

8. The method of claim 7, wherein the at least one transition metal dichalcogenide is dispersed in the aqueous solution.

9. The method of claim 8, wherein the at least one transition metal dichalcogenide is dispersed with at least one surfactant.

10. The method of claim 9, wherein the at least one surfactant is sodium dodecyl sulfate.

* * * * *